(12) United States Patent
Eisenberg et al.

(10) Patent No.: US 11,390,646 B2
(45) Date of Patent: *Jul. 19, 2022

(54) STRUCTURE-BASED PEPTIDE INHIBITORS OF α-SYNUCLEIN AGGREGATION

(71) Applicant: The Regents of the University of California, Oakland, CA (US)

(72) Inventors: David S. Eisenberg, Los Angeles, CA (US); Smriti Sangwan, Los Angeles, CA (US); Lin Jiang, Santa Monica, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 36 days.

This patent is subject to a terminal disclaimer.

(21) Appl. No.: 16/883,515

(22) Filed: May 26, 2020

(65) Prior Publication Data

US 2021/0002329 A1    Jan. 7, 2021

Related U.S. Application Data

(63) Continuation of application No. 16/311,593, filed as application No. PCT/US2017/040106 on Jun. 29, 2017, now Pat. No. 10,815,271.

(60) Provisional application No. 62/356,410, filed on Jun. 29, 2016.

(51) Int. Cl.
| | |
|---|---|
| C07K 7/02 | (2006.01) |
| G01N 33/68 | (2006.01) |
| C07K 14/47 | (2006.01) |
| C07K 7/08 | (2006.01) |
| A61P 25/16 | (2006.01) |
| A61K 38/00 | (2006.01) |

(52) U.S. Cl.
CPC .............. *C07K 7/02* (2013.01); *A61P 25/16* (2018.01); *C07K 7/08* (2013.01); *C07K 14/47* (2013.01); *C07K 14/4711* (2013.01); *G01N 33/6896* (2013.01); *A61K 38/00* (2013.01); *C07K 2319/10* (2013.01); *G01N 2800/2835* (2013.01)

(58) Field of Classification Search
None
See application file for complete search history.

(56) References Cited

FOREIGN PATENT DOCUMENTS

| WO | 0204482 | 1/2002 |
|---|---|---|
| WO | 2009027690 | 3/2009 |

OTHER PUBLICATIONS

Rodriguez, "structure of the toxic core of alpha-synuclein from invisible crystals" Nature, 2015 525: pp. 486-490.
PCT International Preliminary Reporton Patentability (IPRP) dated Jan. 10, 2019 (International Application No. PCT/US17/40106).
Extended European Search Report dated Dec. 3, 2020 for European Patent Application No. 17821295.7.
El-Agnaf, O.M.A., et al., "A strategy for designing inhibitors of a-synuclein aggregation and toxicity as a novel treatment for Parkinson's disease and related disorders", The FASEB Journal • FJ Express, Aug. 2004, pp. 1315-1317, vol. 18, No. 11.
Mongodin, E.F., et al., "Secrets of Soil Survival Revealed by the Genome Sequence of Arthrobacter aurescens TC1", PloS Genetics, Dec. 2006, pp. 2094-2106, vol. 2, No. 12.
Saelices, L., et al., "Uncovering the Mechanism of Aggregation of Human Transthyretin", Journal of Biological Chemistry, Nov. 2015, pp. 28932-28943, vol. 290, No. 48.
Arnau, J., et al., "Current strategies for the use of aYnity tags and tag removal for the purifcation of recombinant proteins", Protein Expression and Purifcation, 2006, pp. 1-13, vol. 48.
Frankel, A.E., et al., "Characterization of diphtheria fusion proteins targeted to the human interleukin-3 receptor", Protein Engineering, 2000, pp. 575-581, vol. 13, No. 8.
Luo, Z., et al., "Fabrication of self-assembling D-form peptide nanofiber scaffold d-EAK16 for rapid hemostasis", Biomaterials, 2011, pp. 2013-2020, vol. 32.
PCT International Search Report & Written Opinion dated Dec. 18, 2017, International Application No. PCT/US17/40106.
Bodles, A. M., et al., "Inhibition of fibril formation and toxicity of a fragment of a-synuclein by an N-methylated peptide analogue", Nieuroscience Letters, 359 (2004) 89-93.
UniProtKB/TrEMBL Accession No. D7W8W4, Oct. 5, 2010 (online). [Retrieved on Nov. 29, 2017]. Retrieved from the internet <URL: http:l/www.uniprot.org/un iprot/D7W8W4 .txt?version 1 > Entire document.

*Primary Examiner* — Adam Weidner
(74) *Attorney, Agent, or Firm* — Gates & Cooper LLP

(57) ABSTRACT

This invention relates to inhibitory peptides which bind to α-synuclein molecules and inhibit α-synuclein amyloidogenic aggregation, α-synuclein cytotoxicity, and spread of α-synuclein. Methods of making and using the inhibitory peptides (e.g. to treat subjects having conditions or diseases that are mediated by α-synuclein, such as Parkinson's disease, dementia with Lewy bodies, or MSA) are described.

20 Claims, 7 Drawing Sheets
(7 of 7 Drawing Sheet(s) Filed in Color)

Specification includes a Sequence Listing.

STRUCTURE-BASED PEPTIDE INHIBITORS OF α-SYNUCLEIN AGGREGATION

CROSS-REFERENCE TO RELATED APPLICATIONS

This application is a continuation application that claims the benefit under 35 U.S.C. § 121 of U.S. patent application Ser. No. 16/311,593, filed Dec. 19, 2018, which is the National Stage of International Application No. PCT/US2017/040106 (International Publication No. WO 2018/005867), filed Jun. 29, 2017, which claims priority under Section 119(e) of U.S. Provisional Patent Application Ser. No. 62/356,410, filed Jun. 29, 2016, entitled "STRUCTURE-BASED PEPTIDE INHIBITORS OF ALPHA-SYNUCLEIN AGGREGATION" the contents of which are incorporated herein by reference.

STATEMENT OF GOVERNMENT SUPPORT

This invention was made with government support under Grant Number AG029430, awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Aug. 9, 2017, is named 30435_305-WO-U2_SL.txt and is 18,456 bytes in size.

BACKGROUND INFORMATION

Parkinson's disease (PD), dementia with Lewy bodies (DLB) and multiple system atrophy (MSA) are together classified as Synucleinopathies, a class of neurodegenerative diseases characterized by the pathological accumulation of the protein, α-synuclein (α-syn) in neuronal cells. Together these make up the second most common form of neurodegenerative disease. The presynaptic protein α-synuclein (α-syn), found in both soluble and membrane-associated fractions of the brain, aggregates in, for example, Parkinson's Disease (PD). These aggregates are the main component of Lewy bodies, the defining histological feature of this neurodegenerative disease, and have been shown to accompany neuronal damage[7]. Without wishing to be bound by any particular mechanism, it is suggested that this and two other observations point to aggregated α-syn as a molecular cause of Parkinson's disease[8]. The first is that families with inherited forms of PD carry mutations in α-syn, such as A53T, and abundant Lewy bodies[9,10,11]. The second is that families with duplicated or triplicated genes encoding α-syn develop early onset PD, presumably because at high local concentrations α-syn is forced into amyloid[12,13].

Based on structural studies, a number of different models for α-syn fibrils have been proposed. Limited proteolysis and NMR studies suggest that the fibril core is composed of residues 30-100 (Miake H (2002) J Biol Chem 277(21): 19213-19219). Crystal structures and NMR studies suggest different models of α-syn fibrils. In one model based on crystal structures of short segments, two monomers per sheet form extended steric zippers (Rodriguez J A, et al. (2015) Nature 525(7570):486-490). In a second ssNMR-based model, a greek key topology with one monomer per amyloid layer has been shown (Tuttle M D, et al. (2016) Nat Struct Mol Biol 23(5):409-415). Taken together these studies suggest that α-syn can form polymorphic fibrillar architectures. The segment 68-78 of α-syn termed NACore may form the core of α-syn fibrils. NACore, resides within the 35-residue NAC (non-amyloid β component) domain found in amyloid deposits (Rodriguez J A, et al. (2015) Nature 525(7570):486-490). NACore aggregates readily, and the aggregates display properties such as diffraction pattern and cytotoxicity similar to full-length α-syn. Additionally, β-synuclein, a homologue does not contain residues 74-84 and is not found in amyloid deposits, and removal of residues 71-82 has been shown previously to reduce the aggregation and toxicity in vitro and in a drosophila model (Giasson et al. (2001) J Biol Chem 276(4):2380-2386 and Periquet et al. (2007) J Neurosci 27(12):3338-3346). Additionally, a modification at Thr72 prevents its aggregation propensity.

The present inventors recently showed that it is possible to efficiently arrest the aggregation of the Alzheimer's Disease related protein Tau and the semen-derived enhancer of HIV virus infection (SEVI) utilizing short amino-acid inhibitors designed to specifically "cap" the growing aggregates (Sievers et al.[36]; U.S. Pat. No. 8,754,034[57]). They also showed that the same design strategy can lead to a designed cell-penetrating peptide that inhibits p53 amyloid formation, rescues mutant p53 function in cancer cell lines and decreases tumor proliferation (US patent application 2014/037387[58]). Accordingly, there is an attractive therapeutic window which targets the α-synuclein amyloid aggregation, major component of intracellular deposits in the form of Lewy bodies (LBs) in Parkinson's disease and related neurodegenerative disorders.

There is a need to identify agents which prevent and/or inhibit α-synuclein aggregation and/or cytotoxicity.

SUMMARY OF THE INVENTION

Although α-syn amyloid formation has been extensively characterized, little headway has been made in developing therapeutics that can inhibit α-syn aggregation or reduce the prion-like spread of α-syn aggregates ("seeds") from cell to cell. Promising approaches include antibodies that sequester α-syn aggregates as well as small molecule stabilizers that bind α-syn monomers (see, e.g. Mandler M, et al. (2015) Mol Neurodegener 10(1). doi:10.1186/s13024-015-0008-9; Wrasidlo W, et al. (2016) Brain:aww238). Using the atomic structure of NACore as a template, we have developed a new class of inhibitors, peptide agents that bind α-syn seeds and prevent their growth and elongation. As shown below, these inhibitors inhibit α-synuclein fibril formation and seeding in a number of model systems, and spread of α-synuclein aggregates.

The invention disclosed herein has a number of embodiments. One embodiment of the invention is a composition of matter comprising at least one inhibitory peptide that inhibits α-synuclein (SEQ ID NO: 1) aggregation by binding to residues 68-78 of α-synuclein. In typical embodiments of the invention, the inhibitory peptide comprises the sequence GAVVWGVTAVKK (SEQ ID NO: 3) or RAVVTGVTAVAE (SEQ ID NO: 4). Optionally the inhibitory peptide comprises the sequence GAVVWGVTAVKKKKK (SEQ ID NO: 5), GAVVWGVTAVKKGRKKRRQRRRPQ (SEQ ID NO: 6); or YGRKKRRQRRRAVVTGVTAVAE (SEQ ID NO: 7). In certain embodiments of the invention, the composition comprises a plurality of inhibitory peptides. Typically, the inhibitory peptide(s) is/are from 6 to 30 amino acids in length.

In the inhibitory peptide compositions of the invention, at least one of the amino acids in the inhibitory peptide may comprise a non-naturally occurring amino acid (e.g. a D-amino acid or an amino acid comprising a N-methyl group moiety); and/or the inhibitory peptide is coupled to a heterologous peptide tag. Such heterologous peptide tags include amino acid sequences that increase peptide solubility; or amino acid sequences that facilitate monitoring or manipulation of the peptide; or amino acid sequences that facilitate peptide entry into a mammalian cell. Optionally these peptide compositions include a pharmaceutically acceptable carrier and a peptide stabilizing excipient.

Another embodiment of the invention is an expression vector encoding an inhibitory peptide that inhibits α-synuclein aggregation by binding to residues 68-78 of α-synuclein. A related embodiment is a kit comprising a peptide inhibits α-synuclein (SEQ ID NO: 1) aggregation by binding to residues 68-78 of α-synuclein or an expression vector encoding such a peptide. Embodiments of the invention also include a method of making a peptide disclosed herein by synthesizing it chemically or producing it recombinantly. Yet another embodiment of the invention is a complex comprising α-synuclein and a peptide that inhibits α-synuclein aggregation by binding to residues 68-78 of α-synuclein.

Yet another embodiment of the invention is a method for reducing or inhibiting α-synuclein (SEQ ID NO: 1) aggregation, comprising contacting α-synuclein amyloid fibrils with an inhibitory peptide disclosed herein in an amount sufficient to reduce or inhibit α-synuclein aggregation. Optionally in this method, the α-synuclein amyloid fibrils are within an in vivo environment. Alternatively in this method, the α-synuclein amyloid fibrils are within an in vitro environment. A related embodiment of the invention is a method of modulating the size or rate of growth of a α-synuclein amyloid fibril, comprising contacting the fibril with an amount of at least one inhibitory peptide that inhibits α-synuclein (SEQ ID NO: 1) aggregation by binding to residues 68-78 of α-synuclein in an environment where the inhibitory peptide contacts residues 68-78 of α-synuclein so that the contacted α-synuclein amyloid fibril exhibits a modulated size or rate of growth.

Yet another embodiment of the invention is a method of observing the presence or absence of α-synuclein amyloid fibrils in a biological sample comprising combining a biological sample with a peptide that binds to residues 68-78 of α-synuclein, allowing the peptide to bind to α-synuclein amyloid fibrils that may be present in the biological sample, and then monitoring this combination for the presence of complexes formed between α-synuclein amyloid fibrils and the peptide; wherein the presence of said complexes show the presence of α-synuclein amyloid fibrils in the biological sample. In this embodiment, one of our inhibitors can be bound to an imaging agent such as a radioactive label, a radio-opaque label, a fluorescent dye, a fluorescent protein, a colorimetric label or the like (e.g. to facilitate an imaging method such as MRI or PET), and our inhibitor will bind to alpha-synuclein fibrils in the brain of a patient, permitting imaging of the fibrils for diagnosis for following disease progression.

Other objects, features and advantages of the present invention will become apparent to those skilled in the art from the following detailed description. It is to be understood, however, that the detailed description and specific examples, while indicating some embodiments of the present invention, are given by way of illustration and not limitation. Many changes and modifications within the scope of the present invention may be made without departing from the spirit thereof, and the invention includes all such modifications.

DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
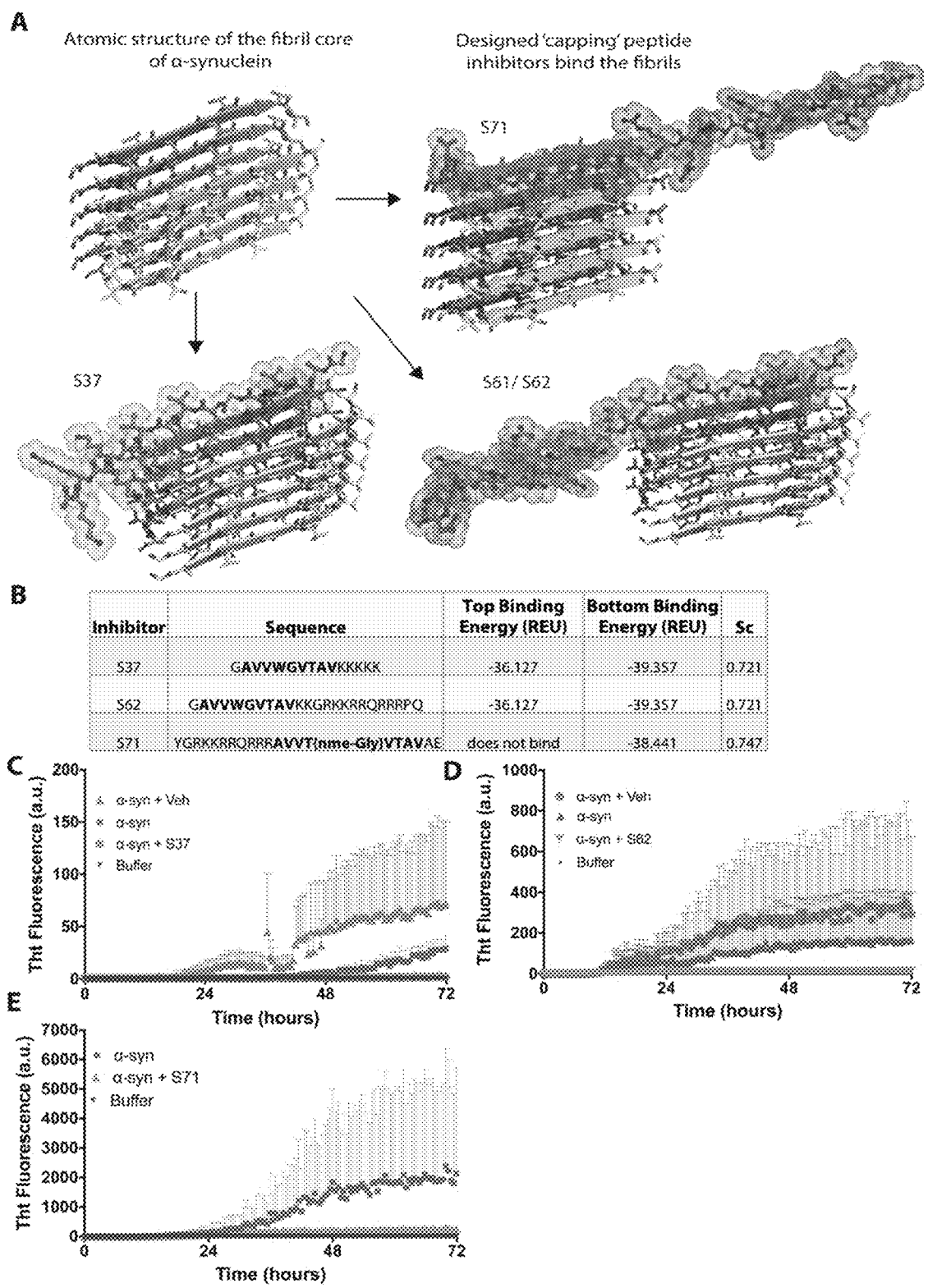
FIG. 1: Design of α-syn seeding inhibitors. (A) Structure based design of α-syn aggregation inhibitors. Structure of NACore is composed of two self complementary β-sheets forming steric zipper. Three types of inhibitors (maroon, orange and cyan) were identified that bind one or both ends. (B) Binding energies of the different inhibitors calculated by Rossetta show S37 and S62 bind both interfaces while S71 is only predicted to bind one interface. Shape complementarity of all three inhibitors is high. (C)-(E) graphed data from Thioflavin T assays measuring α-syn aggregation and the effect of inhibitors. 50 μM α-syn and inhibitors at 5 fold molar excess were added.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. All publications, patents, and patent applications cited herein are hereby incorporated by reference in their entirety for all purposes. In the description of the preferred embodiment, reference may be made to the accompanying drawings which form a part hereof, and in which is shown by way of illustration a specific embodiment in which the invention may be practiced. It is to be understood that other embodiments may be utilized and structural changes may be made without departing from the scope of the present invention.

α-synuclein, a 140 amino acid protein is found in amyloid deposits in neuronal cells in disease conditions. A causative link between α-syn amyloid formation and disease progression is supported by the findings that gene duplications and familial mutations that increase amyloid load also cause early-onset PD, and more than 90% sporadic PD patients stain positive for α-syn deposits. The invention disclosed herein provides a structure-based approach to halt α-syn aggregation. We hypothesized that the atomic structures of NACore and PreNAC are preserved in α-syn amyloid seeds and recruit the endogenous protein into a zipper conformation. Using the atomic structure of NACore, we developed inhibitors that hinder fibril formation and tested their efficacy in vitro and in cell culture. The same procedure can be used to develop inhibitors based on PreNAC. The inhibitors are optimized to cap the ends of the fibril, preventing further addition of monomers. We used the software Rosetta to design peptide sequences that interact favorably with the NACore segment. The energy function used by Rosetta takes into account electrostatic interactions, hydrogen bonding, Van der Waals forces, among other terms to assess binding energy. Once a specific residue has been shown to produce favorable binding in a certain position of the designed peptide, it can be fixed and prevented from further design, while the rest of the sequence is further refined. We performed this process of fixing and redesign iteratively until an optimal set of sequences was identified. This rational design process allowed for computationally sampling of orders of magnitude more inhibitor sequences than what was experimentally feasible to test.

We carried out screens for crystals of peptide segments within the NAC domain and adjacent regions, seeking structural information on the molecular basis of aggregation and toxicity of α-syn. Using the ZipperDB algorithm[55], crystallizable amyloid-forming segments in the NAC domain were identified. In particular, we identified and concentrated on a central segment of α-syn, residues 68-78, which is referred to herein as NACore because of its important role in both the aggregation and cytotoxicity of α-syn, NACore is the fibril-forming core of the 35 residue NAC (Non Amyloid-β Component) domain (residues 61-95) of full, 140 residue α-synuclein. In some studies, we utilized a sub-fragment of NACore, comprised of residues 69-77. In other studies we crystallized and determined the structure of residues 47-56 of α-synuclein termed PreNAC which forms another steric zipper. The identified segments were chemically synthesized and crystallized and their three-dimensional structures were determined by micro-crystallography and micro-electron diffraction (MicroED).

To find the most effective inhibitors, nearly 100 different designs were tested empirically with sequential rounds of optimization on the inhibitor design. For example, we observed that the location of the tag on N or C terminus can affect its efficiency. Additionally, the type of modification added can also affect its efficacy. In our case, only a Trp substitution at Thr72 was effective whereas Arg substitution was not. Although the computational approach is not powerful enough to identify one successful design, it can narrow our search for candidate inhibitors, which can then be refined through rational design.

The efficiency of capping inhibitors in preventing seeding was tested using a cell-based assay. In this system, transfection of nanomolar amounts of α-syn seeds caused endogenous protein aggregation. The aggregates display amyloidogenic properties—binding to amyloid-specific small molecules, faithfully transferred upon cell division and remarkable specificity (Sanders D W, et al. (2014) Neuron 82(6):1271-1288). For example, α-syn fibrils can only seed α-syn protein into aggregates. Notably, in this system we do not observe acute cell death upon formation of aggregates with only a mild slowing of cell proliferation. Our inhibitors prevented puncta formation in this system with a single administration of inhibitors effective for 2-3 days.

Seeding, in the context of amyloid disease, is the sequential transfer of pathologic protein aggregates along connected tissues. This process contributes to progression and severity of neurodegenerative diseases. To date, there are no therapeutics that specifically target seeding, in part, due to lack of information of the structural properties of pathological seeds. The present application relates, e.g., to the design, synthesis and functional characterization of peptides that bind specifically to α-synuclein (α-syn) aggregates and block, inhibit and/or diminish α-syn aggregation and/or α-syn cytotoxicity. The peptide inhibitors specifically "cap" the growing aggregates of α-synuclein. In some embodiments, the peptides are fused to cell penetrating peptides that enhance their delivery into cells.

Apart from the spontaneous aggregation of intracellular α-syn into amyloid fibrils, a second phenomenon that contributes to disease progression is the prion-like spread of α-syn aggregates (Goedert M (2015). Science 349(6248): 1255555-1-1255555-9). Braak staging has shown that pathology gradually spreads over time through connected brain regions, and cell culture and animal models show that small amounts of α-syn aggregates can act as seeds and induce aggregation of the native protein (see, e.g. Braak H, et al. (2003) Neurobiol Aging 24(2):197-211; Braak et al. (2009) Adv Anat Embryol Cell Biol 201:1-119; Masuda-Suzukake M, et al. (2013) Brain 136(4):1128-1138; Desplats P, et al. (2009) Proc Natl Acad Sci USA 106(31):13010-13015; Luk K C, et al. (2009) Proc Natl Acad Sci 106(47): 20051-20056). Although distinct from canonical prions that can be transmitted from person to person, this phenomenon of 'seeding' seems the driver of disease progression.

Patient-extracted fibrils are observed to differ in seeding capacity and display strain-like characteristics. In vitro the PD patient extracted fibrils caused dramatic increase in α-syn aggregation, and in cell culture model the seeded samples increased puncta formation. Notably, unlike previous reports where patient derived α-syn filaments seeds in cell culture, in our assays we did not observe seeding in cell culture (Prusiner S B, et al. (2015) Proc Natl Acad Sci 112(38):E5308-E5317; and Woerman A L, et al. (2015) Proc Natl Acad Sci 112(35):E4949-E4958). Previous reports utilized substantia nigra tissues whereas we used frontal and temporal tissues, which might differ in seeding potency. Indeed in previous reports, fibrils extracted from different brain regions have been shown to differ in seeding capacity reminiscent of different strains (Prusiner S B, et al. (2015) Proc Natl Acad Sci 112(38):E5308-E5317). Furthermore, the different inhibitors varied in efficiency against different seeds. For example, S61 was effective against seeds A and B only whereas S71 was effective against seeds B and D. Recently, an NMR structure of full length α-syn fibrils was reported in which the NACore segment was not found in an extended zipper conformation although the segment 68-78 is found in the core of the fibril (Tuttle M D, et al. (2016) Nat Struct Mol Biol 23(5):409-415). Or it may be that the inhibitors described therein can bind to the conformation of NACore in the NMR structure. Also it is conceivable that the NMR structure and the steric zipper structure are different polymorphs. In the absence of a diagnostic method to identify different polymorphs in human subjects, theoretically a cocktail of different inhibitors targeting different polymorphs could be useful.

We used a combination of computational methods and rational design to develop a line of inhibitors targeted at preventing the spread of α-syn aggregates. Our approach was only made possible by the determination of the atomic structure of the core of α-syn amyloid fibrils, and this approach can be adopted for other diseases where seeding plays a role in disease progression. The inhibitors prevent aggregation of α-synuclein in vitro and in cell culture models. The inhibitors also show efficacy in preventing seeding by patient-derived α-synuclein fibrils both in vitro and in cell culture models. Our results provide evidence that pathological seeds of α-syn contain steric zippers and suggest a therapeutic approach targeted at the spread and progression that may be applicable for PD and related synucleinopathies. Similarly our inhibitors may be applicable for a diagnostic approach for PD and related synucleinopathies.

We hypothesized that mutations, overexpression or other cellular factors can destabilize the native α-synuclein structure, exposing an adhesive, "steric-zipper" segment, proposed as the basic building block of amyloid aggregates[18, 19]. We therefore generated high-resolution views of the amyloid spines of α-synuclein aggregates. We then applied the Rosetta-based method[36] to design inhibitors which specifically "cap" the growing aggregates of α-synuclein and thus disrupt and inhibit further α-synuclein aggregation, using the α-synuclein 69-77 structure or the α-synuclein 68-78 structure as a template.

We utilized the atomic structure of NACore [68-GAVVTGVTAVA-78] (SEQ ID NO: 46) as a template and using computational and structure-based approaches designed peptidic inhibitors. The atomic structure of NACore revealed a pair of self-complementary β-sheets forming a steric zipper (Sawaya M R, et al. (2007) Nature 447(7143):453-457). The inhibitors are predicted by Rossetta-based computational modeling to bind the steric zipper interface and 'cap' the fibrils. We identified 3 candidate inhibitors; S37, S61 and S71 that bind favorably with one or both ends of the zipper (FIG. 1). The binding energies and shape complementarity of the three inhibitors are also favorable (FIG. 1B). All the inhibitors retain most residues of the native sequence of NACore but contain one or more modified residues. Rodriquez et al. showed that a smaller 9-residue segment within NACore [69-AVVTGVTAV-77] (SEQ ID NO: 48) aggregates slower than NACore and the structure is similar to NACore. Rodriguez et al. (2015) also describes a second segment of a-syn, termed PreNAC, with sequence GVVHGVTTV residues 47-56. Designed inhibitors to this sequence might also inhibit fibril formation of a-syn.

In order to prevent the self-aggregation of our designed inhibitors, we used the shorter segment along with one or more modifications. S37 has a W mutation at Thr72 and an additional poly-lysine tag at the C-terminus to induce charge-charge repulsion. It is predicted to bind both tips of the steric zipper fibril. S61 and S62 retain the same inhibitor sequence as S37 but instead of poly-lysine tag, a TAT tag is added to aid solubility and prevent self-aggregation. S71 has a methylated glycine at Gly73 that weakens hydrogen bonding along the β-sheet and an additional TAT tag for solubility and cell penetration.

We tested the efficacy of the inhibitors in an in vitro aggregation assay. Recombinantly purified α-syn was aggregated in the presence of the inhibitors and monitored by measuring fluorescence of Thioflavin T, an amyloid binding dye. All three inhibitors prevented aggregation with a significant reduction in ThT fluorescence (FIG. 1C, 1D, 1E).

Figure 2:
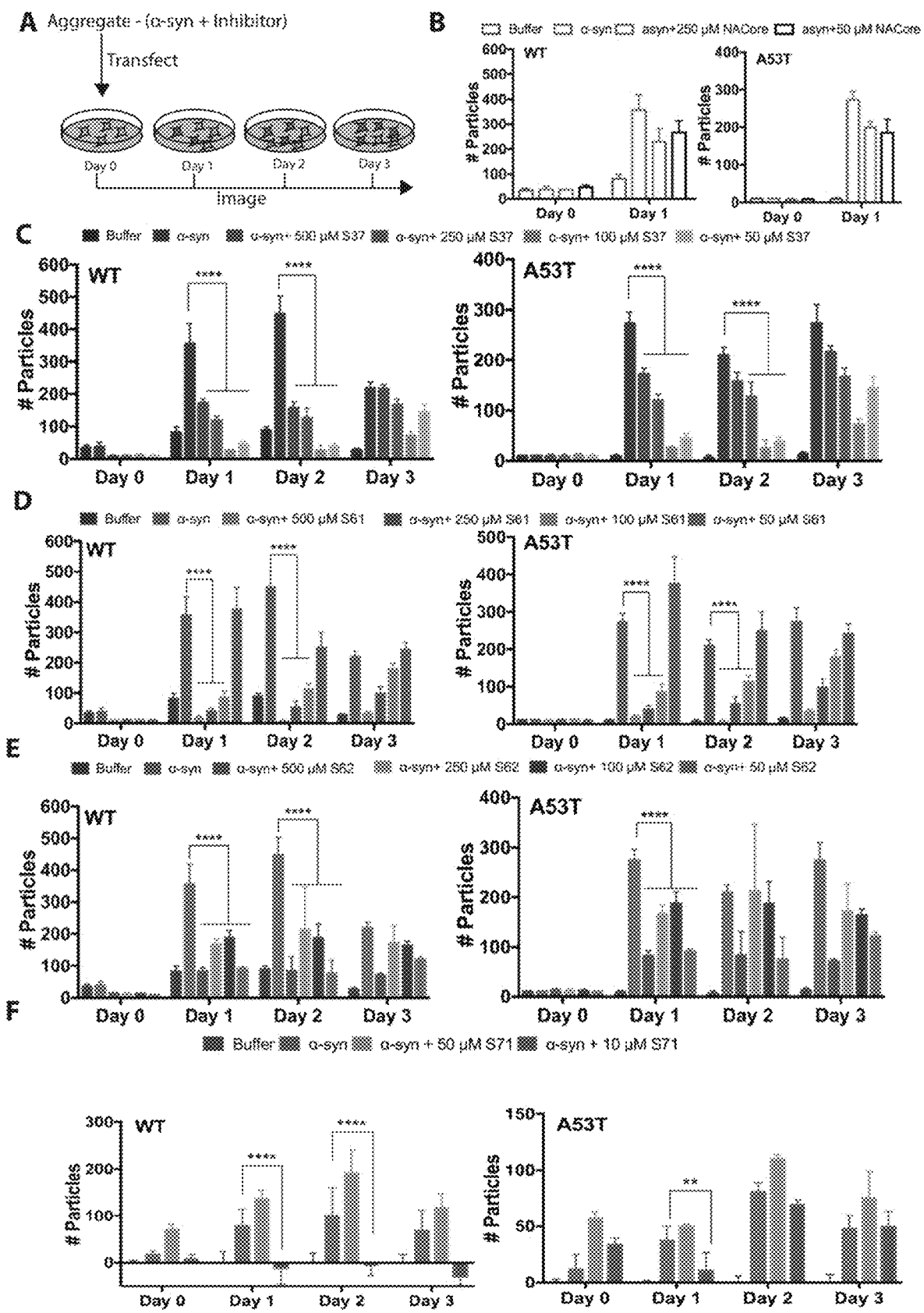
FIG. 2: α-syn aggregates formed in the presence of inhibitors are not seeding competent. (A) Experimental design of cell culture seeding assay. α-syn was aggregated in the presence of inhibitors and the mixture was transfected in HEK293 cells expressing YFP labeled WT α-syn or A53T α-syn (green). A53T is a familial variant of alpha-synuclein which causes early onset Parkinson's disease. Upon transfection endogenous α-syn formed fluorescent puncta (red) (B) NACore does not affect seeding capacity of α-syn fibrils. (C,D,E) 50 μM α-syn aggregated in 10, 5, 2 and 1 fold excess of S37, S61 and S62 was not seeding competent as measured by counting total number of particles formed per well in both WT and A53T expressing cells. (F) 50 μM α-syn aggregated in excess of S71 was not seeding competent as measured by counting total number of particles formed per well in both WT and A53T expressing cells. Results shown as Mean±SD (n=3). Statistical significance was analyzed by two way ANOVA.

We tested the efficacy of the inhibitors in preventing aggregation in a cell culture model. For these assays, we utilized two HEK293T cells that stably express YFP-labeled full-length WT α-syn and A53T α-syn (Sanders D W, et al. (2014) Neuron 82(6):1271-1288). In this model, lipofectamine-mediated transfection of recombinant fibrils leads to aggregation of the endogenous YFP-labeled protein that are seen as fluorescent puncta. Additionally, these puncta increase in size and number over time. This proliferation of aggregates over time is indicative of a 'seeding' phenomenon whereby a small amount of amyloid fibrils induces aggregation of the endogenous protein. First we tested the parent peptide segment, NACore to check its effect on seeding. α-syn was aggregated in the presence of molar excess of NACore (FIG. 2B). The mixture was transfected in cells and puncta formation was visualized and the number of puncta were counted as particles per well. As expected, NACore did not cause a significant reduction in puncta formation in either cell line. Next we aggregated 50 µM α-syn in the presence of 500 µM, 250 µM, 100 µM and 50 µM inhibitor corresponding to 10, 5, 2 and 1 fold excess. The mixture was then transfected in cells and aggregation was monitored over time for up to 3 days by fluorescence imaging (FIG. 2A). S37 caused a significant reduction in seeding for up to 2 days in both WT and A53T expressing cell lines. Similar to S37, S61 (FIG. 2D) also caused a reduction in puncta formation with maximum efficacy at 2, 5 and 10 fold excess in both cell lines. Aggregates formed in the presence of S62 (FIG. 2E) were also seeding incompetent with significantly less particles forming at all inhibitor concentrations. S71 was tested at equimolar and sub-stoichiometric ratios and found to reduce the seeding potency of the aggregates (FIG. 2F). These results suggest that the inhibitors prevent formation of seeding competent aggregates.

We tested the efficacy of the inhibitors to prevent seeding in the cell culture model (FIG. 3A). We transfected the α-syn fibrils along with the different inhibitors. NACore, the parent aggregating peptide did not affect the seeding potency of α-syn fibrils (FIG. 3B). S37 caused significant reduction in seeding in both cell lines at 12.5 µM and 6.25 µM concentrations for up to 2 days (FIG. 3C). S61 at concentrations of 2.5 µM and 1.25 µM caused a prolonged reduction of seeding lasting up to 6 days in WT α-syn cells and 2 days in A53T α-syn HEK cells (FIG. 3D). S62 was effective at concentrations of 12.5 µM and 6.25 µM in both cell lines (FIG. 3E). S71 was effective at low concentrations of 1.25 µM. Interestingly, we observed that addition of higher concentrations of these inhibitors does not prevent seeding suggesting a critical concentration range with maximum efficacy. Together these results suggest that inhibitors can cap fibril seeds and prevent their elongation.

Figure 4:
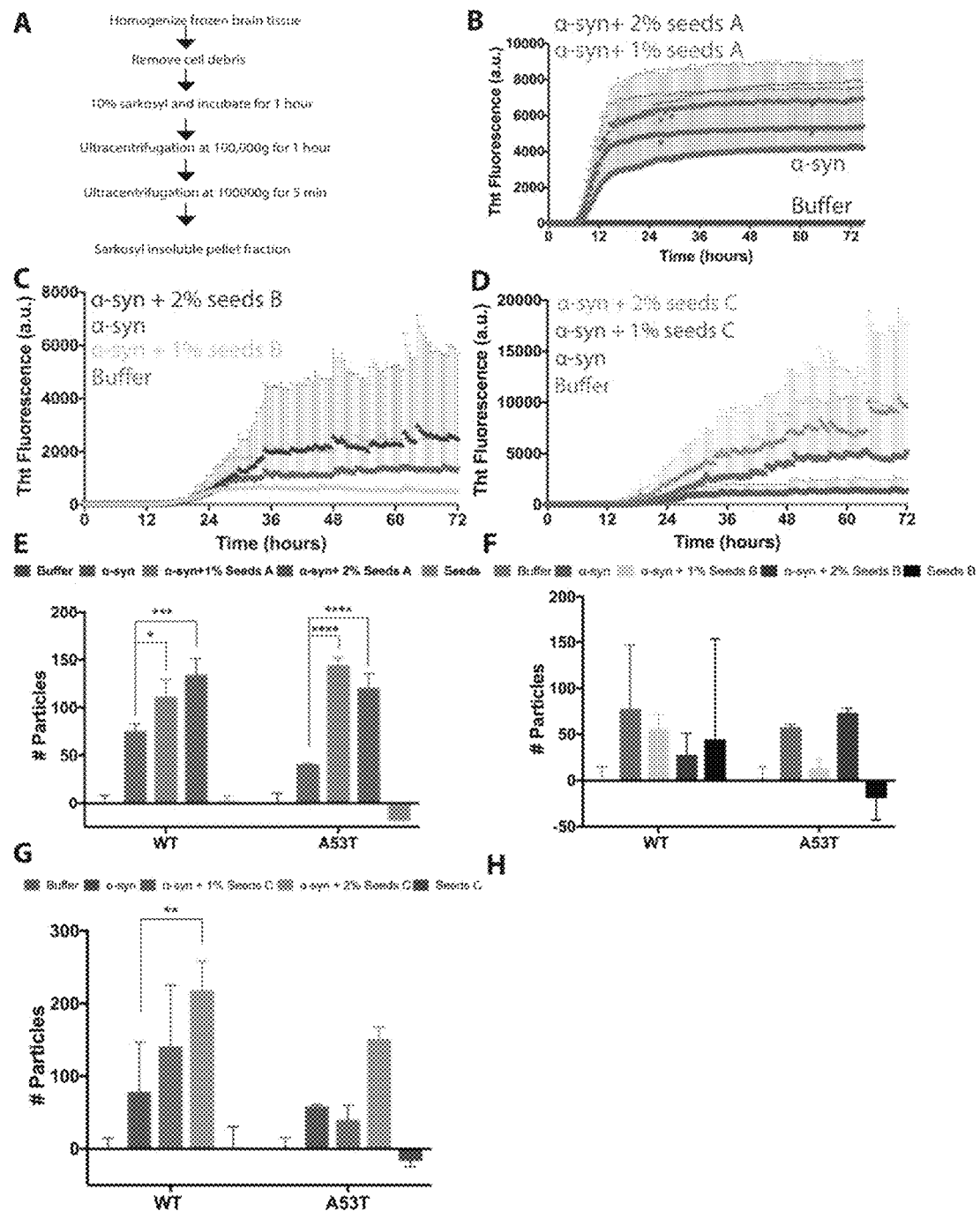
FIG. 4: Extracted filaments from PD brain tissue seed α-syn aggregation in vitro and in cell culture. (A) Protocol for extraction of sarkosyl insoluble protein filaments from PD brain tissues. (B,C,D) 2% seeds from 3 different subjects induce rapid α-syn aggregation with 4-10 fold increase in ThT fluorescence. (E,F,G) α-syn seeded by filaments from PD subjects induce more particles than α-syn alone. All data reported as particles counted per well and normalized to particles counted in buffer treated wells. Results shown as Mean±SD (n=3). Statistical significance was analyzed by two way ANOVA.

We extracted insoluble protein aggregates from frozen autopsy PD brain tissues. We obtained tissues from 4 different subjects including the substantia nigra and frontal regions of one subject and temporal and frontal regions of other subjects. Using previously described protocols (Goedert et al. (1992) Neuron 8(1):159-168) that included precipitation with the ionic detergent sarkosyl, we extracted insoluble protein aggregates (FIG. 4A). All samples robustly seeded α-syn aggregation in vitro and in our cell culture model. In vitro addition of 2% seeds increased the ThT fluorescence 4 to 10 fold (FIG. 4B, 4C, 4D) along with a small decrease in the lag time. The seeded samples were then transfected in HEK cells. Consistent with the ThT assay, all seeded samples induced rapid puncta formation (FIG. 4E, 4F, 4G). Thus, fibrils extracted from PD brain tissues seeds recombinant protein, and the aggregates formed upon seeding induce rapid puncta formation in cell culture.

Figure 5:
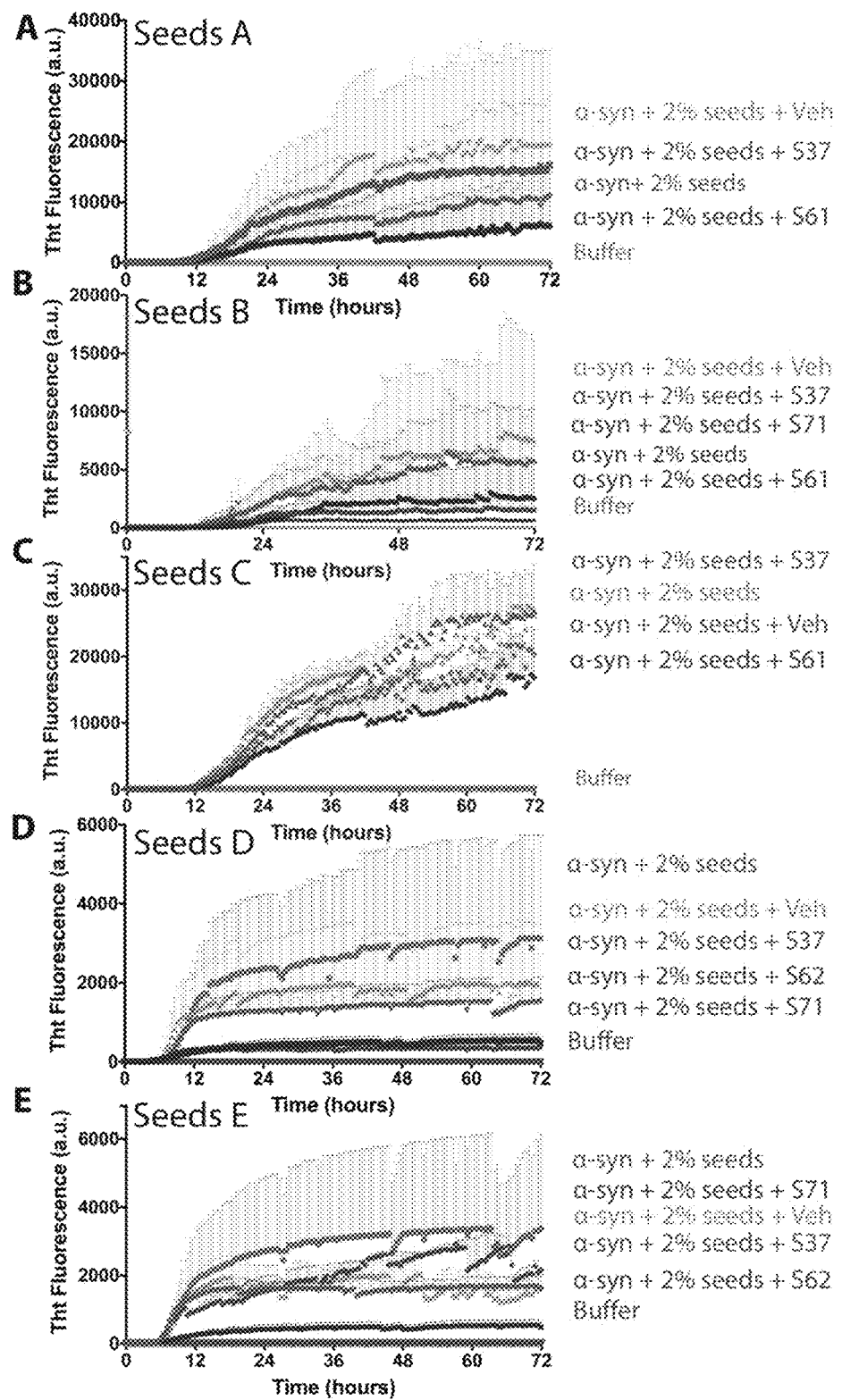
FIG. 5: Inhibitors prevent seeding by PD tissue-extracted filaments. Filaments from 4 different subjects were tested for seeding α-syn aggregation and monitored by ThT assay. S61 and S62 were effective against all seeds that were tested. S71 was effective against seeds B and D.
Figure 6:
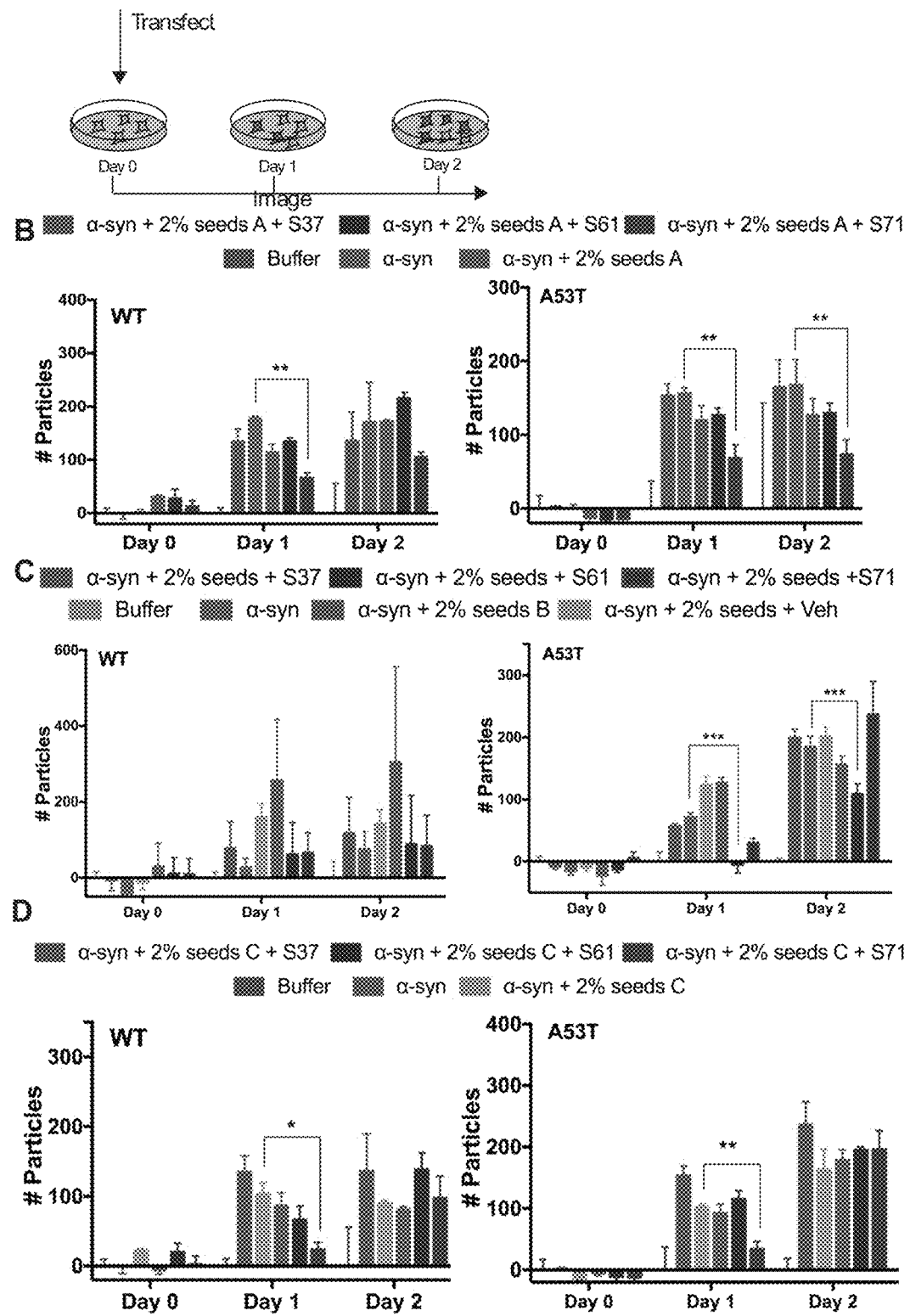
FIG. 6: α-syn fibrils formed in the presence of PD filament seeds and inhibitors are not seeding competent. (A) Experimental design of cell culture seeding assay (B, C, D) Inhibitors were tested for inhibition of seeding by three different PD brain extracted tissues. S71 was effective against all three seeds while S61 was effective against Seeds B. All data reported as particles counted in each well normalized to the particles counted in buffer treated wells. Results shown as Mean±SD (n=3). Statistical significance was analyzed by two way ANOVA.

We tested the effect of the different inhibitors in preventing α-syn aggregation in the presence of PD extracted seeds. S71 and S62 were most effective showing efficacy against all seeds as measured by ThT fluorescence assay (FIG. 5). S61 also reduced aggregation of two different seeds (FIG. 5B, 5D) whereas S37 showed marginal reduction in ThT fluorescence (FIG. 5D). Next we tested the seeding potency of the α-syn aggregates formed in the presence of PD seeds and the different inhibitors (FIG. 6A). Aggregates formed in the presence of S71 (FIGS. 6B, 6C and 6D) did not induce puncta formation in both WT and A53T expressing HEK cells. S61 also showed efficacy (FIG. 6C). Consistent with the in vitro assay, S37 was not effective in reducing the seeding potency of aggregates. Together these results suggest that S62 and S71 can prevent formation of seeding competent fibrils.

Figure 7:
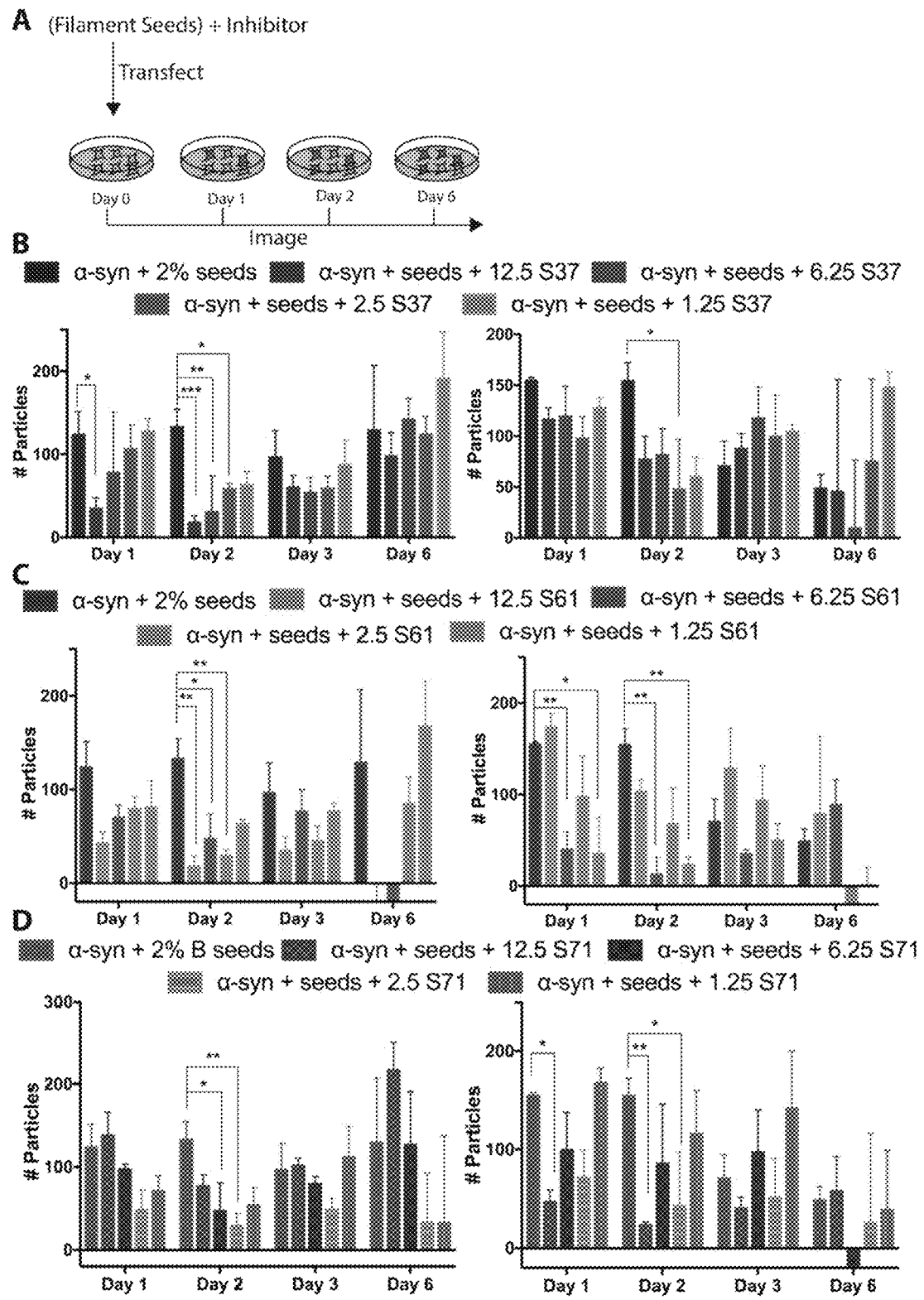
FIG. 7: Inhibitors reduce seeding by PD filament seeded α-syn fibrils in cell culture. (A) Experimental design of cell culture seeding assay. (B,C,D) α-syn fibrils formed in the presence of two different PD related filaments were transfected in YFP-α-syn HEK cells and fluorescence measured thereafter for up to 6 days. S37 prevented seeding at concentrations of 12.5 µM-1.25 µM. S61 prevented seeding with a pronounced effect on Day 2. S71 reduced seeding at concentrations of 6.25 µM. All data reported as number of particles counted per well normalized to particles counted on Day 0 before transfection. Results shown as Mean±SD (n=3). Statistical significance was analyzed by two way ANOVA.

We tested the efficacy of the inhibitors in preventing seeding by PD fibrils in cell culture. α-syn aggregates formed in the presence of PD fibrils were transfected in WT HEK cells along with the different inhibitors (FIG. 7A). S37 prevented puncta formation for up to 2 days for two different PD filaments at concentrations of 12.5 µM-1.25 µM (FIG. 7B). Similar to S37, S61 also showed efficacy for up to 2 days at concentrations of 12.5 µM-1.25 µM, and S71 also prevented seeding at similar concentrations. These results suggest that inhibitors robustly prevent seeding in cell culture.

The disclosure immediately above describes work with a number of working embodiments of the invention. The invention disclosed herein provides such inhibitory peptides; pharmaceutical compositions comprising inhibitory peptides of the invention and a pharmaceutically acceptable carrier; methods of using the inhibitory peptides to block, inhibit and/or prevent α-synuclein aggregation and/or α-synuclein cytotoxicity, comprising contacting an α-synuclein molecule (e.g. a monomer, small aggregate, oligomer, or fibril) with an effective amount of a peptide inhibitor of the invention, or administering to a subject an effective amount of a peptide inhibitor of the invention; and computer-related embodiments, such as a method for designing and obtaining inhibitory peptides or small molecules based on the structures described herein.

Advantages of the inhibitory peptides of the invention include: (1) Synthetic peptides are not expensive. (2) Cell penetration and protein stability are not challenging thanks to their composition and small size. In addition, the peptides can be fused to cell penetrating peptides that enhance their delivery into cells. (3) They are unexpectedly stable: they are not proteolyzed and exhibit a sufficiently long half-life to function in vivo (e.g. in a body). (4) Peptide inhibitors are specific for their targets, and therefore present fewer opportunities for side effects than, e.g., small molecules, which may bind to many targets.

The invention disclosed herein has a number of embodiments. One embodiment of the invention is a composition of matter comprising at least one inhibitory peptide that inhibits α-synuclein (SEQ ID NO: 1) aggregation by binding to residues 68-78 of α-synuclein. As disclosed in the Examples below, working embodiments of these peptides include S37, S62 and S71 as shown in Table 1 below:

| Inhibitor | Sequence |
|---|---|
| S37 | GAVVWGVTAVKKKKK |
| S62 | GAVVWGVTAVKKGRKKRRQRRRPQ |
| S71 | YGRKKRRQRRRAVVT{N-me-Gly}VTAVAE |

In the table N-me-Gly stands for Glycine with a methylated amino group. Bold type gives the inhibitor sequence. Unbold type shows tags, either solubilizing tags or linkers.

In typical embodiments of the invention, the inhibitory peptide comprises the sequence GAVVWGVTAVKK (SEQ ID NO: 3) or RAVVTGVTAVAE (SEQ ID NO: 4). Optionally the inhibitory peptide comprises the sequence GAVVWGVTAVKKKKK (SEQ ID NO: 5), GAVVWGVTAVKKGRKKRRQRRRPQ (SEQ ID NO: 6); or YGRKKRRQRRRAVVTGVTAVAE (SEQ ID NO: 7). In certain embodiments of the invention, the composition comprises a plurality of inhibitory peptides. Typically, the inhibitory peptide(s) is/are from 6 to 30 amino acids in length. Active variants of any of these inhibitory peptides are also included. Inhibitory peptides having the preceding sequences, including the active variants, are sometimes referred to herein as "inhibitory peptides of the invention."

In the inhibitory peptide compositions of the invention, at least one of the amino acids in the inhibitory peptide comprises a non-naturally occurring amino acid (e.g. a D-amino acid or an amino acid comprising a N-methyl group moiety); and/or the inhibitory peptide is coupled to a heterologous peptide tag. Such heterologous peptide tags include amino acid sequences that increase peptide solubility in vivo or in vitro (e.g. a plurality of arginine residues); or amino acid sequences that facilitate monitoring or manipulation of the peptide in vivo or in vitro (a plurality of lysine or histidine amino acids); or amino acid sequences that facilitate peptide entry into a mammalian cell (e.g. a cell penetrating peptide sequence). Another aspect of the invention is a pharmaceutical composition comprising an inhibitory peptide of the invention and a pharmaceutically acceptable carrier. Such pharmaceutical compositions are sometimes referred to herein as "pharmaceutical compositions of the invention." Optionally the peptide compositions disclosed herein include a pharmaceutically acceptable carrier and a peptide stabilizing excipient.

Another embodiment of the invention is an expression vector encoding an inhibitory peptide that inhibits α-synuclein aggregation by binding to residues 68-78 of α-synuclein. Optionally, the expression vector is one used to deliver polypeptides to mammalian cells such as a lentivirus. In this context, another embodiment of the invention is a method of delivering a DNA encoding an inhibitory peptide that inhibits α-synuclein aggregation in a mammalian cell (e.g. an ex vivo or in vivo cell) by contact the mammalian cell with a vector that transduces the cell so that the DNA is expressed in the cell.

Another embodiment is kit comprising a peptide inhibits α-synuclein (SEQ ID NO: 1) aggregation by binding to residues 68-78 of α-synuclein or an expression vector encoding such a peptide. Embodiments of the invention also include a method of making a peptide disclosed herein by synthesizing it chemically or producing it recombinantly. Yet another embodiment of the invention is a complex comprising α-synuclein and a peptide that inhibits α-synuclein aggregation by binding to residues 68-78 of α-synuclein.

Another embodiment is a peptide designed on the structure of PreNAC (residues 47-56 of α-synuclein: GVVHGVTTVA) to inhibit fibril formation of α-synuclein.

Yet another embodiment of the invention is a method for reducing or inhibiting α-synuclein (SEQ ID NO: 1) aggregation, comprising contacting α-synuclein amyloid fibrils with an inhibitory peptide disclosed herein in an amount sufficient to reduce or inhibit α-synuclein aggregation. Optionally in this method, the α-synuclein amyloid fibrils are within an in vivo environment. Alternatively in this method, the α-synuclein amyloid fibrils are within an in vitro environment. A related embodiment of the invention is a method of modulating the size or rate of growth of a α-synuclein amyloid fibril, comprising contacting the fibril with an amount of at least one inhibitory peptide that inhibits α-synuclein (SEQ ID NO: 1) aggregation by binding to residues 68-78 of α-synuclein in an environment where the inhibitory peptide contacts residues 68-78 of α-synuclein so that the contacted α-synuclein amyloid fibril exhibits a modulated size or rate of growth.

The peptide inhibitors disclosed herein can be used as a therapy to halt the spread of Parkinson's disease within the brain. Alternatively, the peptide inhibitors disclosed herein can be used as a diagnostic probe to recognize pathological aggregated seeds of the protein, α-synuclein in diseases such as Parkinson's disease, dementia with Lewy bodies and multiple system atrophy. In this context, embodiments of the invention include methods of observing aggregated seeds of the protein, α-synuclein in a biological sample, comprising contacting the biological sample with a peptide that binds to residues 68-78 of α-synuclein, and then observing if the peptide binds to aggregated seeds of the protein, α-synuclein, if present in that biological sample. Typically in these methods, a heterologous peptide tag is coupled to the inhibitory peptide in order to facilitate observation of the peptide. Optionally in these methods, the biological sample is from an individual suspected of suffering from Parkinson's disease, dementia with Lewy bodies or multiple system atrophy.

As used herein, the singular forms "a," "an," and "the" include plural referents unless the context clearly dictates otherwise. For example, in the preceding case, the pharmaceutical composition may comprise one or more inhibitory peptide molecules of the invention, which can be the same or different.

Another aspect of the invention is a complex comprising an α-synuclein molecule (e.g. a monomer, small aggregate, oligomer, or fibril of α-synuclein) and an inhibitory peptide of the invention. They may be bound to, conjugated with, or otherwise associated with each other. The α-synuclein and the inhibitory peptide may be covalently or non-covalently linked.

Other aspects of the invention include a polynucleotide encoding an inhibitory peptide of the invention; an expression vector comprising the polynucleotide; a cell transfected with the polynucleotide or the expression vector; and a method for making the peptide, comprising expressing it in the transfected cell, cultivating the cell and harvesting the peptide thus generated.

Another aspect of the invention is a method for inhibiting (preventing, stopping) aggregation of an α-synuclein molecule (e.g. a monomer, small aggregate, oligomer, or fibril of α-synuclein), comprising contacting the α-synuclein molecule with an effective amount of an inhibitory peptide or pharmaceutical composition of the invention. The α-synuclein molecule can be in solution or in a cell, which is in culture or in a subject. In one embodiment, the contacting of an α-synuclein molecule which is a monomer, oligomer or small aggregate prevents aggregation (oligomerization, further oligomerization, and/or fibril formation) of the α-synuclein molecule. In another embodiment, the contacting of an aggregated form of α-synuclein or a fibril prevents further aggregation (fibrillization) of the aggregated form or the fibril.

In one embodiment of this method, the α-synuclein protein molecule which is contacted is in a subject having a disease or condition which is mediated by the presence of fibrillated α-synuclein (sometimes referred to herein as an α-synuclein-mediated disease or condition, or a synucleinopathy) such as, e.g., Parkinson's disease (PD), Lewy body dementia and multiple system atrophy. α-synuclein pathologies are also found in other related neurodegenerative diseases, such as, e.g., both sporadic and familial Alzheimer's disease.

Another aspect of the invention is a method for treating a subject having an α-syn-mediated disease or condition, such as, e.g., Parkinson's disease, Lewy body dementia, or multi system atrophy, comprising administering to the subject an effective amount of an inhibitory peptide or pharmaceutical composition of the invention. The treatment can result in the blockage (prevention) or inhibition of α-synuclein aggregation and/or α-synuclein cytotoxicity in the subject, and spread of pathology (seeding).

Another aspect of the invention is a computer-implemented method for identifying a peptide that inhibits α-synuclein aggregation and/or α-synuclein cytotoxicity as described herein. Another aspect of the invention is a kit comprising an inhibitory peptide of the invention, optionally packaged in a container. Another aspect of the invention is a method for making an inhibitory peptide of the invention, comprising synthesizing it chemically or producing it recombinantly.

Yet another embodiment of the invention is a method of observing the presence or absence of α-synuclein amyloid fibrils in a biological sample comprising combining a biological sample with a peptide that binds to residues 68-78 of α-synuclein, allowing the peptide to bind to α-synuclein amyloid fibrils that may be present in the biological sample, and then monitoring this combination for the presence of complexes formed between α-synuclein amyloid fibrils and the peptide; wherein the presence of said complexes show the presence of α-synuclein amyloid fibrils in the biological sample. Optionally in this method, the presence of complexes formed between α-synuclein amyloid fibrils and the peptide is monitored using a detectable label that is coupled to the peptide (e.g. a heterologous peptide tag). In illustrative embodiments of the invention, the peptide comprises the sequence GAVVWGVTAVKK (SEQ ID NO: 3) or RAVVTGVTAVAE (SEQ ID NO: 4). Typically, the method is performed on a biological sample obtained from an individual suspected of suffering from Parkinson's disease. Such embodiments of the invention can be used, for example, in diagnostic methods designed to observe the presence or status of PD, for example to detect disease beginnings before clinical symptoms, and to follow the effectiveness (or lack of effectiveness), of a therapeutic treatment.

Peptide inhibitors of the invention bind specifically (selectively, preferentially) to α-synuclein rather than to unintended proteins. The protein to which the peptide inhibitor binds may be, e.g., a monomer, small aggregate, oligomer, or fibril. For example, the binding can be 2 times, 5 times, 10 times, 100 times or 200 times stronger, or no binding at all can be detected to an unintended target. Conventional methods can be used to determine the specificity of binding, such as e.g. competitive binding assays or other suitable analytic methods.

Active variants of the inhibitory peptides described above are also included. An "active variant" is a variant which retains at least one of the properties of the inhibitory peptides described herein (e.g., the ability to bind to α-synuclein and/or to block, inhibit or prevent α-synuclein fibrillation (aggregation) and/or α-synuclein cytotoxicity). Fibrilization, as used herein, refers to the formation of fiber or fibrils, such as amyloid fibrils.

Suitable active variants include peptidomimetic compounds (any compound containing non-peptidic structural elements that is capable of mimicking the biochemical and/or biological action(s) of a natural mimicked peptide, including, for example, those designed to mimic the structure and/or binding activity (such as, for example, hydrogen bonds and hydrophobic packing interactions) of the peptides according to the methods disclosed herein). Inhibitory peptides of the invention, including active variants thereof, are sometimes referred to herein as "peptidic compounds" or "compounds."

In one embodiment, active variants of the inhibitory peptides are shortened by 1-3 (e.g., 1, 2 or 3) amino acids at either the N-terminus, the C-terminus, or both of the starting inhibitory peptide. In another embodiment, the active variants are lengthened (extended) by 1, 2, 3 or 4 amino acids at the C-terminal end of the starting inhibitory peptide, e.g. with amino acid residues at the position in which they occur in α-synuclein.

A variety of other types of active variants are included. In some embodiments, amino acids other than the ones noted above are substituted. These amino acids can help protect the peptide inhibitors against proteolysis or otherwise stabilize the peptides, and/or contribute to desirable pharmacodynamic properties in other ways. In some embodiments, the non-natural amino acids allow an inhibitor to bind more tightly to the target because the side chains optimize hydrogen bonding and/or apolar interactions with it. In addition, non-natural amino acids offer the opportunity of introducing detectable markers, such as strongly fluorescent markers which can be used, e.g., to measure values such as inhibition constants. Also included are peptide mimetics, such as, e.g., peptoids, beta amino acids, N-ethylated amino acids, and small molecule mimetics.

In one embodiment, non-natural amino acids are substituted for amino acids in the sequence. More than 100 non-natural amino acids are commercially available. These include, for example,

| Non-natural amino acids which can substitute for LEU: | |
|---|---|
| L-cyclohexylglycine | 161321-36-4 |
| L-phenylglycine | 102410-65-1 |
| 4-hydroxy-D-phenylglycine | 178119-93-2 |
| L-α-t-butylglycine | 132684-60-7 |
| cyclopentyl-Gly-OH | 220497-61-0\ |
| L-2-indanylglycine | 205526-39-2 |

| Non-natural amino acids which can substitute for THR: | |
|---|---|
| Thr(tBu)-OH | 71989-35-0 |
| (RS)-2-amino-3-hydroxy-3-methylbutanoic acid | 105504-72-1 |

| Non-natural amino acids which can substitute for ILE: | |
|---|---|
| allo-Ile-OH | 251316-98-0 |
| N-Me-allo-Ile-OH | 136092-80-3 |
| Homoleu-OH | 180414-94-2 |

| Non-natural amino acids which can substitute for ARG: | |
|---|---|
| Nω-nitro-L-arginine | 58111-94-7 |
| L-citrulline | 133174-15-9 |

| Non-natural amino acids which can substitute for TYR: | |
|---|---|
| 3-amino-L-tyrosine | 726181-70-0 |
| 3-nitro-L-tyrosine | 136590-09-5 |
| 3-methoxy-L-tyrosine | |
| 3-iodo-L-tyrosine | 134486-00-3 |
| 3-chloro-L-tyrosine | 478183-58-3 |
| 3,5-dibrimo-L-tyrosine | 201484-26-6 |

| Non-natural amino acids which can substitute for LYS: | |
|---|---|
| Lys(retro-Abz-)-OH | 159322-59-5 |
| Lys(Mca)-OH | 386213-32-7 |
| (Nδ-4-methyltrityl)-L-ornithine | 343770-23-0 |
| N-α--N-ε-(d-Biotin)-L-lysine | 146987-10-2 |

In another embodiment, one or more (e.g. 1, 2, 3, 4, 5, 6, 7, 8, 9, 10, 11, 12, 13, 14, 15, 16 or 17) of the L-amino acids are substituted with a D amino acid.

In another embodiment, one or more (e.g. 1, 2, 3, 4, 5, 6, 7, 8, 9, 10, 11, 12, 13, 14, 15, 16 or 17) N-methylated residues are included in the peptide.

An inhibitory peptide of the invention can comprise, e.g., L-amino acids, D-amino acids, non-natural amino acids, or combinations thereof.

Active variants include molecules comprising various tags at the N-terminus or the C-terminus of the peptide. For example, an inhibitory peptide of the invention can comprise as tags at its N-terminus and/or at its C-terminus: 1, 2, 3, 4, 5, 6, 7, 8, 9 or 10 or more Lysine residues; 1, 2, 3, 4, 5, 6, 7, 8, 9 or 10 or more Arginine residues; 1, 2, 3, 4, 5, 6, 7, 8, 9 or 10 or more Glutamate residues; 1, 2, 3, 4, 5, 6, 7, 8, 9 or 10 or more Aspartate residues; combinations of these amino acid residues; or other polar tags that will be evident to a skilled worker. Other active variants include mutations of the α-synuclein sequence which increase affinity of the inhibitory peptides for the α-synuclein.

In one embodiment, the inhibitor is a small molecule which has been designed by the methods described by Jiang et al.[63] (which is incorporated herein by reference, particularly with regard to this method), using the atomic structure of the fiber forming segment of α-synuclein described herein as the basis for designing the inhibitor. Suitable small molecules that can be identified by this method of Jiang et al. will be evident to a skilled worker.

In one embodiment of the invention, a peptide of the invention is modified so that 1, 2 or 3 of its amino acids are substituted with an amino acid having a non-naturally occurring side chain, such as the non-natural amino acids discussed above, or with an amino acid having a side chain modified by cross-linking (e.g., through the epsilon amino group of a Lys residue) of a small molecule which has been designed by Jiang et al.[63]. Some representative fiber-binding molecules are shown below. These active variants not only cap growing aggregates of α-synuclein but also, via the modified side chains, may bind to (clamp against) the sides of the steric zipper, thereby enhancing the inhibitory activity of the peptide.

Fiber-binding compounds designed by Jiang et al.[63] include:

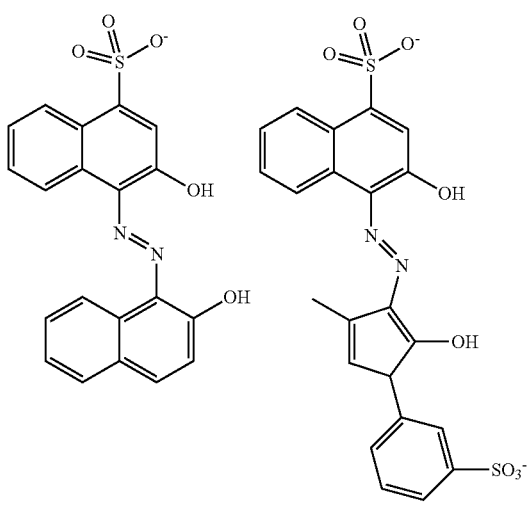

In one embodiment of the invention, an inhibitory peptide of the invention is isolated or purified, using conventional techniques such as the methods described herein. By "isolated" is meant separated from components with which it is normally associated, e.g., components present after the peptide is synthesized. An isolated peptide can be a cleavage product of a protein which contains the peptide sequence. A "purified" inhibitory peptide can be, e.g., greater than 90%, 95%, 98% or 99% pure.

In one embodiment, to enhance the cell permeability of an inhibitory peptide of the invention, the peptide is fused to any of a variety of cell penetrating peptides (CPPs). CPPs typically have an amino acid composition that either contains a high relative abundance of positively charged amino acids such as lysine or arginine or has sequences that contain an alternating pattern of polar/charged amino acids and non-polar, hydrophobic amino acids. These two types of structures are referred to as polycationic or amphipathic, respectively. A third class of CPP's are the hydrophobic peptides, containing only apolar residues, with low net charge or have hydrophobic amino acid groups that are crucial for cellular uptake. Some typical CPP's that can be fused to an inhibitory peptide of the invention are provided in Table 2.

TABLE 2

| Name | Sequence |
|---|---|
| | Reference - original or review |
| polyARG | nR where 4 < n < 17 (e.g., n = 5, 6, 7, 8, 9, 10, 11, 12, 13, 14, 15 or 16) (SEQ ID NO: 8) |
| | Wender, P. A., Mitchell, D. J., Pattabiraman, K., Pelkey, E. T., Steinman, L., and Rothbard, J. B. (2000). The design, synthesis, and evaluation of molecules that enable or enhance cellular uptake: peptoid molecular transporters. Proc. Natl. Acad. Sci. U.S.A. 97, 13003-8. |
| polyLYS | nK where 4 < K < 17 (e.g., K = 5, 6, 7, 8, 9, 10, 11, 12, 13, 14, 15 or 16) |
| D-polyARG | nR where 4 < n < 17 (e.g., n = 5, 6, 7, 8, 9, 10, 11, 12, 13, 14, 15 or 16) |
| D-polyLYS | nK where 4 < K < 17 (e.g., K = 5, 6, 7, 8, 9, 10, 11, 12, 13, 14, 15 or 16) |
| SynB1 | RGGRLSYSRRRFSTSTGR (SEQ ID NO: 9) |
| SynB3 | RRLSYSRRRF (SEQ ID NO: 10) |

TABLE 2-continued

| Name | Sequence |
|---|---|
| | Reference - original or review |

Penetratin RQIKIWFQNRRMKWKK (SEQ ID NO: 11)

Derossi, D., Johot, A. H., Chassaing, G., and Prochiantz, A. (1994). The third helix of the Antennapedia homeodomain translocates through biological mem-branes. J. Biol. Chem. 269, 10444-50.

PenArg RQIRIWFQNRRMRWRR (SEQ ID NO: 12)

PenLys KQIKIWFQNKKMKWKK (SEQ ID NO: 13)

TatP59W GRKKRRQRRRPWQ (SEQ ID NO: 14)

Tat(48-60) GRKKRRQRRRPPQ (SEQ ID NO: 15)

Vives, E., Brodin, P., and Lebleu, B. (1997). A truncated HIV-1 Tat protein basic domain rapidly translocates through the plasma membrane and accumulates in the cell nucleus. J. Biol. Chem. 272, 16010-7.

R9-Tat GRRRRRRRRRPPQ (SEQ ID NO: 16)

Futaki, S. (2002) Arginine-rich peptides: potential for intracellular delivery of macromolecules and the mystery of the translocation mechanisms. Int. J. Pharm. 245, 1-7.

Tat YGRKKRRQRRR (SEQ ID NO: 17)

Vives, E., Brodin, P., and Lebleu, B. (1997). A truncated HIV-1 Tat protein basic domain rapidly translocates through the plasma membrane and accumulates in the cell nucleus. J. Biol. Chem. 272, 16010-7.

D-Tat GRKKRRQRRRPPQ (SEQ ID NO: 18)

Futaki, S. (2002) Arginine-rich peptides: potential for intracellular delivery of macromolecules and the mystery of the translocation mechanisms. Int. J. Pharm. 245, 1-7.

BMVGag(7-25) KMTRAQRRAAARRNRWTAR (SEQ ID NO: 19)

Futaki, S. (2002) Arginine-rich peptides: potential for intracellular delivery of macromolecules and the mystery of the translocation mechanisms. Int. J. Pharm. 245, 1-7.

FHVCoat(35-49) RRRRNRTRRNRRRVR (SEQ ID NO: 20)

Futaki, S. (2002) Arginine-rich peptides: potential for intracellular delivery of macromolecules and the mystery of the translocation mechanisms. Int. J. Pharm. 245, 1-7.

HTLV-II Rex(4-16) TRRQRTRRARRNR (SEQ ID NO: 21)

Futaki, S. (2002) Arginine-rich peptides: potential for intracellular delivery of macromolecules and the mystery of the translocation mechanisms. Int. J. Pharm. 245, 1-7.

P22 N-(14-30) NAKTRRHERRRKLAIER (SEQ ID NO: 22)

pVEC LLIILRRRIRKQAHAHSK (SEQ ID NO: 23)

Elmquist, A., Lindgren, M., Bartfai, T., and Langel, Ü. (2001). VE-cadherin-derived cell-penetrating peptide, pVEC, with carrier functions. Exp. Cell Res. 269, 237-44.

Transportan GWTLNSAGYLLGKINLKALAALAKKIL (SEQ ID NO: 24)

Pooga, M., Hällbrink, M., Zorko, M., and Langel, Ü. (1998). Cell penetration by transportan. FASEB J. 12, 67-77.

TP10 AGYLLGKINLKALAALAKKIL (SEQ ID NO: 25)

Soomets, U., Lindgren, M., Gallet, X., Hällbrink, M., Elmquist, A., Balaspiri, L., Zorko, M., Pooga, M., Brasseur, R., and Langel, Ü. (2000). Dele-tion analogues of transportan. Biochim. Biophys. Acta 1467, 165-76.

PTD-4 PIRRRKKLRRLK (SEQ ID NO: 26)

PTD-5 RRQRRTSKLMKR (SEQ ID NO: 27)

Pep-1 ac-KETWWETWWTEWSQPKKKRKV-cya (SEQ ID NO: 28)

TABLE 2-continued

| Name | Sequence |
|---|---|
| | Reference - original or review |
| Pep-2 | ac-KETWFETWFTEWSQPKKKRKV-cya (SEQ ID NO: 29) |

Morris, M C, Chaloin, L, Choob, M, Archdeacon, J, Heitz, F and Divita, G (2004). Combination of a new generation of PNAs with a peptide-based carrier enables efficient targeting of cell cycle progression. Gene Ther 11: 757-764.

| | |
|---|---|
| Pep-3 | ac-KWFETWFTEWPKKRK-cya (SEQ ID NO: 30) |

Morris, M C, Gros, E, Aldrian-Herrada, G, Choob, M, Archdeacon, J, Heitz, F et al. (2007). A non-covalent peptide-based carrier for in vivo delivery of DNA mimics. Nucleic Acids Res 35: e49.

| | |
|---|---|
| E N(1-22) | MDAQTRRRERRAEKQAQWKAAN (SEQ ID NO: 31) |
| B 21 N-(12-29) | TAKTRYKARRAELIAERR (SEQ ID NO: 32) |
| U2AF(142-153) | SQMTRQARRLYV (SEQ ID NO: 33) |
| PRP6(129-144) | TRRNKRNRIQEQLNRK (SEQ ID NO: 34) |
| MAP | KLALKLALKLALALKLA (SEQ ID NO: 35) |
| SBP | MGLGLHLLVLAAALQGAWSQPKKKRKV (SEQ ID NO: 36) |
| FBP | GALFLGWLGAAGSTMGAWSQPKKKRKV (SEQ ID NO: 37) |
| MPG | ac-GALFLGFLGAAGSTMGAWSQPKKKRKV-cya (SEQ ID NO: 38) |

Morris, M C, Vidal, P, Chaloin, L, Heitz, F and Divita, G (1997). A new peptide vector for efficient delivery of oligonucleotides into mammalian cells. Nucleic Acids Res 25: 2730-2736.

| | |
|---|---|
| MPG(ΔNLS) | ac-GALFLGFLGAAGSTMGAWSQPKSKRKV-cya (SEQ ID NO: 39) |
| REV(34-50) | TRQARRNRRRRWRERQR (SEQ ID NO: 40) |

Futaki, S. (2002) Arginine-rich peptides: potential for intracellular delivery of macromolecules and the mystery of the translocation mechanisms. Int. J. Pharm. 245, 1-7.

ACPPs from Jiang et al., PNAS 2004 - lower case indicates D-aa. The symbol "_" in some of these sequences indicates a position at which any of a variety of art-recognized protease cleavage sites can be inserted:

| | |
|---|---|
| | EEEEEDDDDK_AXRRRRRRRRRXC (SEQ ID NO: 41) |
| | EEEEEDDDDK_ARRRRRRRRRXC (SEQ ID NO: 42) |
| | EDDDDK_AXRRRRRRRRRXC (SEQ ID NO: 43) |
| | EEDDDDK_ARXRRXRRXRRXRXC (SEQ ID NO: 44) |
| | DDDDDDK_ARRRRRRRRRXC (SEQ ID NO: 45) |

In another embodiment, the CPP is polyD(1-16).

In general, it is advisable that the length of the CPP is rather short, e.g. less than about 30 amino acids, in order to improve stability and pharmacodynamic properties once the molecule enters a cell.

In some embodiments, the CPP is directly attached (fused) to a peptide of the invention. In other embodiments, it is desirable to separate the highly charged CPP from the inhibitor peptide with a linker, to allow the inhibitor to retain its activity. Any of a variety of linkers can be used. The size of the linker can range, e.g., from 1-7 or even more amino acids (e.g., 1, 2, 3, 4, 5, 6 or 7 amino acids). For example, the linker can be QVTNVG at the N-terminus and QKTVEG at the C-terminus or a truncated version thereof having 1, 2, 3, 4 or 5 of the contiguous amino acids N-terminal to the inhibitory peptide.

In embodiments of the invention, the inhibitory peptide is detectably labeled. Labeled peptides can be used, e.g., to better understand the mechanism of action and/or the cellular location of the inhibitory peptide. Suitable labels which enable detection (e.g., provide a detectable signal, or can be detected) are conventional and well-known to those of skill in the art. Suitable detectable labels include, e.g., radioactive active agents, fluorescent labels, and the like. Methods for attaching such labels to a protein, or assays for detecting their presence and/or amount, are conventional and well-known.

An inhibitory peptide of the invention can be synthesized (e.g., chemically or by recombinant expression in a suitable host cell) by any of a variety of art-recognized methods. In order to generate sufficient quantities of an inhibitory peptide for use in a method of the invention, a practitioner can, for example, using conventional techniques, generate nucleic acid (e.g., DNA) encoding the peptide and insert it into an expression vector, in which the sequence is under the control of an expression control sequence such as a promoter or an enhancer, which can then direct the synthesis of the peptide. For example, one can (a) synthesize the DNA de novo, with suitable linkers at the ends to clone it into the vector; (b) clone the entire DNA sequence into the vector; or (c) starting with overlapping oligonucleotides, join them by conventional PCR-based gene synthesis methods and insert the resulting DNA into the vector. Suitable expression vectors (e.g., plasmid vectors, viral, including phage, vectors, artificial vectors, yeast vectors, eukaryiotic vectors, etc.) will be evident to skilled workers, as will methods for making the vectors, inserting sequences of interest, expressing the proteins encoded by the nucleic acid, and isolating or purifying the expressed proteins.

Another aspect of the invention is a pharmaceutical composition comprising one or more of the inhibitory peptides and a pharmaceutically acceptable carrier. The components of the pharmaceutical composition may be detectably labeled, e.g. with a radioactive or fluorescent label, or with a label, for example one that is suitable for detection by positron emission spectroscopy (PET) or magnetic resonance imaging (MRI). For example, peptides of the invention can be coupled to a detectable label selected from the group consisting of a radioactive label, a radio-opaque label, a fluorescent dye, a fluorescent protein, a colorimetric label, and the like. In some embodiments, the inhibitory peptide is present in an effective amount for the desired purpose.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use. For example, "pharmaceutically acceptable salts" of a compound means salts that are pharmaceutically acceptable, as defined herein, and that possess the desired pharmacological activity of the parent compound.

Another aspect of the invention is a polynucleotide encoding an inhibitory peptide of the invention. In embodiments of the invention, the polynucleotide is operably linked to a regulatory control sequence (e.g., a promoter or an enhancer) to facilitate production of the encoded protein following introduction (e.g. by transfection) into a suitable cell. Other embodiments include a cell comprising the expression vector; and a method of making an inhibitory peptide of the invention comprising cultivating the cell and harvesting the peptide thus generated.

As used throughout this application, "about" means plus or minus 5% of a value.

Another aspect of the invention is a kit for carrying out any of the methods described herein. The kit may comprise a suitable amount of an inhibitory peptide of the invention; reagents for generating the peptide; reagents for assays to measure their functions or activities; or the like. Kits of the invention may comprise instructions for performing a method. Other optional elements of a kit of the invention include suitable buffers, media components, or the like; a computer or computer-readable medium providing the structural representation of a crystal structure described herein; containers; or packaging materials. Reagents for performing suitable controls may also be included. The reagents of the kit may be in containers in which the reagents are stable, e.g., in lyophilized form or stabilized liquids. The reagents may also be in single use form, e.g., in single reaction form for administering to a subject.

Characterization of candidate inhibitory peptides of the invention can be carried out by any of a variety of conventional methods. For example, the peptides can be assayed for the ability to reduce or inhibit α-synuclein aggregation or cytotoxicity or cell-to-cell spread. The assays can be carried out in vitro or in vivo. Suitable assays will be evident to a skilled worker; some suitable assays are described herein.

One aspect of the invention is a method for reducing or inhibiting α-synuclein aggregation, comprising contacting α-synuclein protofilaments with an effective amount of one or more of the inhibitory peptides of the invention. Such a method can be carried out in solution or in a cell (e.g. cells in culture or in a subject).

Another aspect of the invention is a method for treating a subject having a disease or condition which is mediated by the presence of fibrillated α-synuclein (sometimes referred to herein as an α-synuclein-mediated disease or condition), comprising administering to the subject an effective amount of an inhibitory peptide or pharmaceutical composition of the invention. Among such diseases or conditions are, e.g., Parkinson's disease (PD), Lewy body dementia, or multiple system atrophy. Another aspect of the invention is a method to prevent the onset of such diseases or conditions (e.g., PD), or to treat a subject in the early stages of such diseases or conditions, or that is developing such a disease or condition, in order to prevent or inhibit development of the condition or disease.

An inhibitory peptide or pharmaceutical composition of the invention is sometimes referred to herein as an "inhibitor."

An "effective amount" of an inhibitor of the invention is an amount that can elicit a measurable amount of a desired outcome, e.g. inhibition of α-synuclein aggregation or cytotoxicity; for a diagnostic assay, an amount that can detect a target of interest, such as an α-synuclein aggregate; or in a method of treatment, an amount that can reduce or ameliorate, by a measurable amount, a symptom of the disease or condition that is being treated.

A "subject" can be any subject (patient) having aggregated (fibrillated) α-synuclein molecules associated with a condition or disease which can be treated by a method of the present invention. In one embodiment of the invention, the subject has PD. Typical subjects include vertebrates, such as mammals, including laboratory animals, dogs, cats, non-human primates and humans.

The inhibitors of the invention can be formulated as pharmaceutical compositions in a variety of forms adapted to the chosen route of administration, for example, orally, nasally, intraperitoneally, or parenterally, by intravenous, intramuscular, topical or subcutaneous routes, or by injection into tissue.

Suitable oral forms for administering the inhibitors include lozenges, troches, tablets, capsules, effervescent tablets, orally disintegrating tablets, floating tablets designed to increase gastric retention times, buccal patches, and sublingual tablets.

The inhibitors of the invention may be systemically administered, e.g., orally, in combination with a pharmaceutically acceptable vehicle such as an inert diluent or an assimilable edible carrier, or by inhalation or insufflation. They may be enclosed in coated or uncoated hard or soft shell gelatin capsules, may be compressed into tablets, or may be incorporated directly with the food of the patient's diet. For oral therapeutic administration, the compounds may be combined with one or more excipients and used in the form of ingestible tablets, buccal tablets, troches, capsules, elixirs, suspensions, syrups, wafers, and the like. For compositions suitable for administration to humans, the term "excipient" is meant to include, but is not limited to, those ingredients described in Remington: The Science and Practice of Pharmacy, Lippincott Williams & Wilkins, 21st ed. (2006) (hereinafter Remington's).

The inhibitors may be combined with a fine inert powdered carrier and inhaled by the subject or insufflated. Such compositions and preparations should contain at least 0.1% compounds. The percentage of the compositions and preparations may, of course, be varied and may conveniently be between about 2% to about 60% of the weight of a given unit dosage form.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. A syrup or elixir may contain the active compound, sucrose or fructose as a sweetening agent, methyl and propylparabens as preservatives, a dye and flavoring such as cherry or orange flavor.

Various other materials may be present as coatings or to otherwise modify the physical form of the solid unit dosage form. For instance, tablets, pills, or capsules may be coated with gelatin, wax, shellac or sugar and the like. Of course, any material used in preparing any unit dosage form should be pharmaceutically acceptable and substantially non-toxic in the amounts employed.

In addition, the inhibitors may be incorporated into sustained-release preparations and devices. For example, the inhibitors may be incorporated into time release capsules, time release tablets, and time release pills. In some embodiments, the composition is administered using a dosage form selected from the group consisting of effervescent tablets, orally disintegrating tablets, floating tablets designed to increase gastric retention times, buccal patches, and sublingual tablets.

The inhibitors may also be administered intravenously or intraperitoneally by infusion or injection. Solutions of the inhibitors can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the compounds which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants.

Sterile injectable solutions are prepared by incorporating the compounds in the required amount in the appropriate solvent with various of the other ingredients enumerated above, as required, followed by filter sterilization. In the case of sterile powders for the preparation of sterile injectable solutions, the preferred methods of preparation are vacuum drying and freeze drying techniques, which yield a powder of the active ingredient plus any additional desired ingredient present in the previously sterile-filtered solutions.

For topical administration, the compounds may be applied in pure form. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Other solid carriers include conventional nontoxic polymeric nanoparticles or microparticles. Useful liquid carriers include water, alcohols or glycols or water/alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Useful dosages of the peptides or pharmaceutical compositions of the invention can be determined by comparing their in vitro activity, and in vivo activity in animal models. Methods for the extrapolation of effective dosages in mice, and other animals, to humans are known to the art.

For example, the concentration of the compounds in a liquid composition, such as a lotion, can be from about 0.1-25% by weight, or from about 0.5-10% by weight. The concentration in a semi-solid or solid composition such as a gel or a powder can be about 0.1-5% by weight, or about 0.5-2.5% by weight.

Effective dosages and routes of administration of agents of the invention are conventional. The exact amount (effective dose) of the agent will vary from subject to subject, depending on, for example, the species, age, weight and general or clinical condition of the subject, the severity or mechanism of any disorder being treated, the particular agent or vehicle used, the method and scheduling of administration, and the like. A therapeutically effective dose can be determined empirically, by conventional procedures known to those of skill in the art. See, e.g, The Pharmacological Basis of Therapeutics, Goodman and Gilman, eds., Macmillan Publishing Co., New York. For example, an, effective dose can be estimated initially either in cell culture assays or in suitable animal models. The animal model may also be used to determine the appropriate concentration ranges and routes of administration. Such information can then be used to determine useful doses and routes for administration in humans. A therapeutic dose can also be selected by analogy to dosages for comparable therapeutic agents.

The particular mode of administration and the dosage regimen will be selected by the attending clinician, taking into account the particulars of the case (e.g., the subject, the disease, the disease state involved, and whether the treatment is prophylactic). Treatment may involve daily or multi-daily doses of compound(s) over a period of a few days to months, or even years.

In general, however, a suitable dose will be in the range of from about 0.001 to about 100 mg/kg, e.g., from about 0.01 to about 100 mg/kg of body weight per day, such as above about 0.1 mg per kilogram, or in a range of from about 1 to about 10 mg per kilogram body weight of the recipient per day. For example, a suitable dose may be about 1 mg/kg, 5 mg/kg, 10 mg/kg, 20 mg/kg, or 30 mg/kg of body weight per day.

The inhibitors are conveniently administered in unit dosage form; for example, containing 0.05 to 10000 mg, 0.5 to 10000 mg, 5 to 1000 mg, or about 100 mg of active ingredient per unit dosage form. In some embodiments, the dosage unit contains about 0.1 mg, about 0.5 mg, about 1 mg, about 10 mg, about 25 mg, about 50 mg, about 75 mg, or about 100 mg, of active ingredient.

EXAMPLES

Example I—The Toxic Core of α-Synuclein of Parkinson's Disease: Structure From Invisible Crystals We carried out screens for crystals of peptide segments within the NAC domain and adjacent regions, seeking structural information on the molecular basis of aggregation and toxicity of α-syn.

Extensive crystal screens of two segments, NACore, residues $^{68}$GAVVTGVTAVA$^{78}$ (SEQ ID NO:46), and PreNAC, $^{47}$GVVHGVTTVA$^{56}$ (SEQ ID NO:47), seemingly produced non-crystalline, amorphous aggregates. But on examination by electron microscopy, we found the aggregates to be clusters of elongated nanocrystals only 50-300 nm in cross section and thus invisible by conventional light microscopy. We confirmed well-ordered crystallinity of NACore at both the SACLA and LCLS free electron lasers. We also found that a 9-residue fragment within the NACore, which we term SubNACore, $^{69}$AVVTGVTAV$^{77}$ (SEQ ID NO:48), yielded crystals 1,000-10,000 times larger in volume than the NACore nanocrystals. We were therefore able to apply synchrotron methods[18,19] to these larger crystals to determine the structure of the amyloid-like fibrils. Although this 9-residue fragment is missing only two residues compared with NACore, it is not as toxic[20], offering insight described below, into the toxicity of α-syn.

To determine the structure of the invisible crystals of NACore and PreNAC, we turned to MicroED[21]. In MicroED an extremely low dose electron beam is directed on a nanocrystal within a transmission electron microscope under cryogenic conditions, yielding diffraction patterns. At the wavelength used in our experiments at 200 keV is very small (0.025 Å) the Ewald sphere is essentially flat yielding diffraction patterns that closely resemble a 2D slice through 3D reciprocal space. As the crystal is continuously rotated in the beam, a series of such diffraction patterns is collected[5]. Scaling together diffraction data collected from multiple crystals produces a full 3D diffraction dataset. MicroED has been successfully applied to the well-known structures of hen egg-white lysozyme[6,5], bovine liver catalase[22] and Ca2+-ATPase[23]. But NACore and PreNAC are the first previously unknown structures determined by MicroED.

For NACore and PreNAC, we collected electron diffraction patterns from nanocrystals that lay preferentially oriented, flat on the surface of a holey carbon Quantifoil grid, in a frozen-hydrated state. Grids were first screened for appropriately sized crystals, and candidate crystals screened for diffraction. We used crystals showing strong diffraction for data collection by continuous unidirectional rotation about a fixed axis, acquiring a series of diffraction frames at fixed time intervals[5]. The needle-shaped crystals typically exceeded the length needed for diffraction; those that were unbent and 100 to 300 nm wide produced the best diffraction patterns. Data from multiple crystals were integrated, scaled and merged together.

The multi-crystal NACore and PreNAC datasets were phased by molecular replacement, using the atomic model of SubNACore and an ideal beta strand model, respectively, as probes. Diffraction phases calculated from the SubNACore probe structure and NACore structure factors yielded a difference density map, which clearly reveals the positions of the missing residues, after subsequent refinement, two water molecules, and several hydrogen atoms. Full models of NACore and PreNAC were refined against the MicroED data, producing structures at 1.4 Å resolution with acceptable R-factors. Electron scattering factors were used in the refinement calculations[24].

Figure 3:
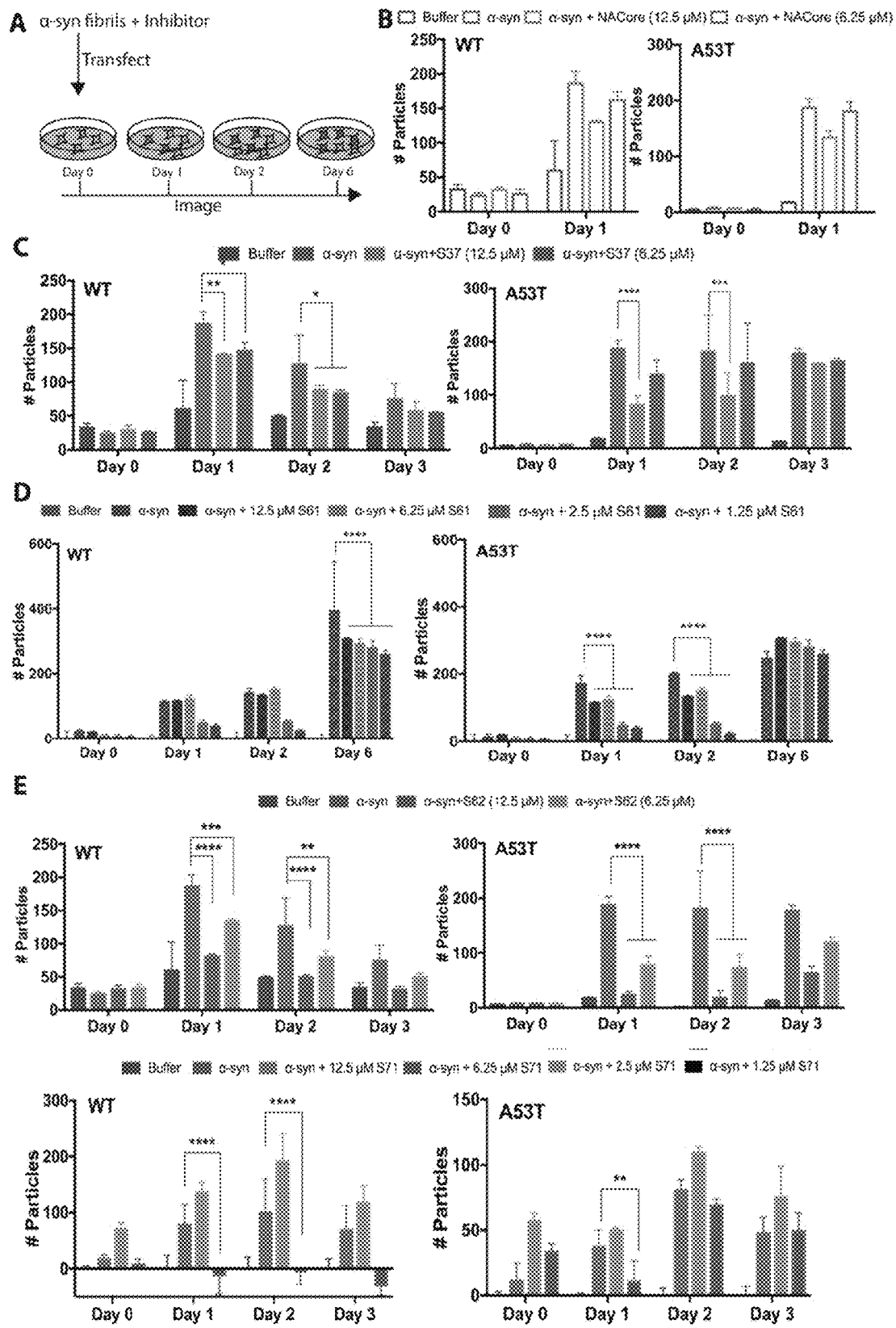
FIG. 3: Inhibitors prevent seeding in cell culture. (A) Experimental design of cell culture seeding assay. 125 nM recombinant α-syn fibrils were transfected with different amounts of inhibitors and aggregation monitored over time. (B) NACore does not affect seeding capacity (C, D, E) S37, S61, S62 and S71 reduce seeding capacity of α-syn. All data reported as particles counted per well and normalized to particles counted in buffer treated wells. Results shown as Mean±SD (n=3). Statistical significance was analyzed by two way ANOVA.

The structure of the NACore peptide chain is a nearly fully extended β-strand. These NACore strands stack in-register into β-sheets, as had been predicted by site-directed spin labeling[25,26]. The sheets are paired, as is usual in amyloid spines, and the pairs of sheets form typical steric-zipper protofilaments, previously seen as the spines in many amyloid-like fibrils formed from short segments of fibril-forming proteins. The unusual features of this steric zipper are that the 11-residue width of the zipper is longer than we have previously observed, and each pair of sheets contains two water molecules, each associated with a threonine sidechain, within the interface instead of being completely dry. Also, in our crystals of NACore, each sheet forms two snug interfaces: Interface A with 268 Å2 of buried accessible surface area per chain, is more extensive and presumably stronger than Interface B (167 Å2), because the terminal residues of the chains in opposing sheets bend towards each other. The structure of PreNAC reveals a peptide chain that forms a β-strand kinked at residue glycine 51. These strands are arranged into pairs of β-sheets that like the NACore structure interdigitate to form steric zipper protofilaments (FIG. 3). Of special note, a five residue segment of PreNAC ($^{51}$GVTTV$^{55}$) (SEQ ID NO:49), differs in only one residue from a five residue segment of NACore ($^{73}$GVTAV$^{77}$) (SEQ ID NO:50), and their backbones and identical sidechains superimpose closely with an alpha carbon RMS deviation of 1.5 Å. This means that weaker interface B of NACore mimics a hypothetical interface between NACore and PreNAC. Below we suggest the significance of the possible contact between these two segments of α-syn.

The relevance of the structure of NACore to fibrils of full length α-syn is established by the resemblance of their diffraction patterns. Specifically, the fiber diffraction pattern of aligned fibrils of full-length and N-terminally acetylated[27] α-syn protein display the same principal peaks as the diffraction of aligned NACore nanocrystals. All three fibrils display the strong reflection at 2.4 Å in their diffraction patterns. This reflection arises in NACore because one β-sheet of the steric zipper is translated along the fiber axis with respect to the other β-sheet by 2.4 Å, one half the 4.8 Å spacing between β-strands, permitting the two sheets to interdigitate tightly together. All three share a strong 4.6 Å reflection, which in NACore results from both the stacking of β-strands and the staggering between adjacent β-sheets of the steric zipper, while a shared reflection at near 8.2 Å likely arises from the distance between the adjacent pairs of β-sheets that make up the α-syn fibril. This comparison of fiber diffraction patterns strongly suggests that the structure of NACore is similar to the spine of our toxic fibrils of full α-syn.

The combined structures of NACore and PreNAC allow us to construct a speculative model for much of the ordered segments of the A53T early onset mutant α-syn. Experimental support of this model comes from the agreement of its simulated fiber diffraction with the measured diffraction patterns of α-syn and N-acetyl α-syn fibrils as well as aligned NACore nanocrystals. Above we noted that the weaker Interface B of NACore mimics a hypothetical interaction of PreNAC with NACore. In fact, the interacting sidechains in the weaker NACore Interface B (G73, T75, and V77) are identical to the sidechains (G51, T53, V55) interacting in the hypothetical interface of PreNAC with NACore.

The identity and structure of the cytotoxic amyloid formed by α-syn remains a subject of intensive research[17,28,29,30,31,32]. The weight of evidence over the past decade has tilted scientific opinion from the fully developed amyloid fibrils found in Lewy bodies as the toxic entities to smaller, transient amyloid oligomers. Yet recently, quantitative arguments have been put forward in favor of fibrils[33]. Without wishing to be bound by any particular mechanism, it is suggested that our experiments of the cytotoxicity of NACore on neuroblastoma cells are consistent with the view that fibrils are toxic: we find that NACore shaken and aggregated for 72 hours displays abundant fibrils, is more toxic than freshly dissolved NACore and is comparably toxic to similarly aggregated full α-syn. We also find greater cytotoxicity of NACore than SubNACore, which is shorter by two residues. This is consistent with the more rapid fibril formation of NACore than of SubNACore. These observations do not rule out the formation of a non-fibrillar, oligomeric assembly, present, but invisible, in our aggregated samples of NACore and α-syn. Of course, NACore is merely a fragment of full length α-syn, and lacks most of the membrane-binding motifs of the N-terminus of the protein which have been implicated in membrane disruption[34,35]. Yet it is clear that NACore is the minimum entity that recapitulates all the features of full length a-syn aggregation and toxicity.

The miniscule size of NACore is typical of amyloid crystals and also of various other biological crystals of interest. For amyloid crystals, our speculation is that the tiny size is a consequence of the natural twist of β-sheets that form the protofilaments of the fibrils. The crystal lattice restrains the twist, creating a strain in these crystals, which increases as crystals grow. Eventually this strain prevents further addition of β-strands, limiting the thickness of the needle crystals. In our experience, longer segments (for example, 11 residues compared to 9 residues) limit crystal growth even more; in the case of 11-residue NACore and 10-residue PreNAC, the strain produces nanocrystals, invisible by optical microscopy. These crystals are too small for mounting and conventional synchrotron data collection, but are ideally suited for analysis by MicroED. Our structures of NACore and PreNAC demonstrate that MicroED is capable of determining new and accurate structures of biological material at atomic resolution. This finding paves the path for applications of MicroED to other biological substances of importance, for which only nanocrystals can be grown. In our particular application, we have been able to learn the atomic arrangement of the core of the crucial NAC domain. This opens opportunities for structure-based design of inhibitors of amyloid formation of α-syn[36].

Methods

Crystallization

Microcrystals of SubNACore, $^{69}$AVVTGVTAV$^{77}$ (SEQ ID NO:48), were grown from synthetic peptide purchased from CS Bio. Crystals were grown at room temperature by hanging drop vaporization. Lyophilized peptide was dissolved in water at 2.9 mg/ml concentration in 48 mM lithium hydroxide. Peptide was mixed in a 2:1 ratio with reservoir containing 0.9 M ammonium phosphate, and 0.1M sodium acetate pH 4.6.

Nanocrystals of NACore, $^{68}$GAVVTGVTAV$^{78}$ (SEQ ID NO:46), were grown from synthetic peptide purchased from CS Bio. Ten batches of synthesized peptide (CSBio) at a concentration of 1 mg/ml in sterile water were shaken at 37° C. on a Torrey Pines orbital mixing plate at speed setting 9, overnight. The insoluble material was washed in 30% (w/v) glycerol then stored in water at room temperature before diffraction. The sample contained a mixture of fibrils and crystals.

Nanocrystals of PreNAC, $^{47}$GVVHGVTTVA$^{56}$ (SEQ ID NO:47), were grown from synthetic peptide purchased from InnoPep. Crystallization trials of synthesized peptide were prepared in batch. Peptide was weighed and dissolved in sterile-filtered 50 mM phosphate buffer pH 7.0 with 0.1% DMSO at a concentration of 5 mg/ml. This solution was shaken at 37° C. on a Torrey Pines orbital mixing plate at speed setting 9, overnight.

Data Collection and Processing

X-ray diffraction data from microcrystals of SubNACore were collected using synchrotron radiation at the Advanced Photon Source, Northeast Collaborative Access Team microfocus beamline 24-ID-E. The beamline was equipped with an ADSC Quantum 315 CCD detector. Data from a single crystal were collected in 5° wedges at a wavelength of 0.9791 Å using a 5 μm beam diameter. We used data from three different sections along the needle axis. The crystals were cryo-cooled (100 K) for data collection. Data were processed and reduced using Denzo/Scalepack from the HKL suite of programs[37].

X-ray diffraction data from nanocrystals of NACore were collected using XFEL radiation at the CXI instrument (Coherent X-ray Imaging) at the Linear Coherent Light Source (LCLS)-SLAC. The photon energy of the X-ray pulses was 8.52 keV (1.45 Å). Each 40 fs pulse contained up to 6×1011 photons at the sample position taking into account a beamline transmission of 60%. The diameter of the beam was approximately 1 μm. We used a concentration of approximately 25 μl of pelleted material suspended in 1 mL water. The sample was injected into the XFEL beam using a liquid jet injector and a gas dynamic virtual nozzle[38]. The micro jet width was approximately 4 μm and the flow rate was 40 μl/min. The sample caused noticeable sputtering of the liquid jet. XFEL data were processed using cctbx.xfel[39,40].

Electron diffraction data from nanocrystals of NACore and PreNAC were collected using MicroED techniques[5,6]. These nanocrystals typically clump together. To break up the clumps, an approximately 100 μL volume of nanocrystals was placed in a sonication bath for 30 minutes. Nanocrystals were deposited onto a quantifoil holey-carbon EM grid in a 2-3 μl drop after appropriate dilution, which optimized for crystal density on the grid. All grids were then blotted and vitrified by plunging into liquid ethane using a Vitrobot Mark IV (FEI), then transferring to liquid nitrogen for storage. Frozen hydrated grids were transferred to a cryo-TEM using a Gatan 626 cryo-holder. Diffraction patterns and crystal images were collected using an FEG-equipped FEI Tecnai F20 TEM operating at 200 kV and recorded using a bottom mount TVIPS F416 CMOS camera with a sensor size of 4000 squared pixels, each 15.6 μm in size per square dimension. Diffraction patterns were recorded by operating the detector in rolling shutter mode with 2×2 pixel binning, producing a final image 2000 squared pixels in size. Individual image frames were taken with exposure times of 3-4 seconds per image, using a selected area aperture with an illuminating spot size of approximately one micron. This geometry equates to an electron dose of less than 0.1 e-/Å2 per second. During each exposure, crystals were continuously rotated within the beam at a rate of 0.3° per second, corresponding to 1.2° wedge per frame. Diffraction data were collected from several crystals each oriented differently with respect to the rotation axis. These data sets each spanned wedges of reciprocal space ranging from 40° to 80°.

Calibration of the sample to detector distance was accomplished using a polycrystalline gold standard and by referencing the prominent reflections in the electron diffraction experiment with the corresponding reflections in the XFEL data. Calibration of the x/y locations of the 64-tile CSPAD detector was performed by cctbx.xfel by refining the optically measured tile positions against a thermolysin data set[39].

To gain compatibility with conventional X-ray data processing programs, the diffraction images were converted from tiff or TVIPS format to the SMV crystallographic format. We used XDS to index the diffraction images[41], and XSCALE for merging and scaling together data sets originating from different crystals. For NACore, data from four crystals were merged, while for PreNAC, data from three crystals were merged to assemble the final data sets.

Structure Determination

The molecular replacement solution for SubNACore was obtained using the program Phaser 42. The search model consisted of a geometrically ideal β-strand composed of nine alanine residues. Crystallographic refinements were performed with the program REFMAC[43]. The molecular replacement solution for NACore was obtained using the program Phaser 42. The search model consisted of the SubNACore structure determined previously. Crystallographic refinements were performed with the program Phenix[44]. The molecular replacement solution for PreNAC was obtained using the program Phaser[42]. The search model consisted of a geometrically ideal β-strand composed of six residues with sequence GVTTVA. Crystallographic refinements were performed with the program Phenix[44].

Model building for all segments was performed using COOT[45]. The coordinates of the final models and the structure factors have been deposited in the Protein Data Bank with PDB code 4RIK for SubNACore, 4RIL for NACore, and 4ZNN for PreNAC. The structures were illustrated using Pymol[46].

α-Synuclein

The human wild type α-syn construct was previously characterized[47] (pRK172, ampicillin, T7 promoter) with sequence:

```
                                        (SEQ ID NO: 1)
MDVFMKGLSKAKEGVVAAAEKTKQGVAEAAGKTKEGVLYVGSKTKEGV

VHGVATVAEKTKEQVTNVGGAVVTGVTAVAQKTVEGAGSIAAATGFVK

KDQLGKNEEGAPQEGILEDMPVDPDNEAYEMPSEEGYQDYEPEA.
```

α-Synuclein Purification

Full length α-syn was purified according to published protocols[31]. The α-syn construct was transformed into *E. coli* expression cell line BL21 (DE3) gold (Agilent Technologies, Santa Clara, Calif.) for wild type α-syn protein expression. A single colony was incubated into 100 mL LB Miller broth (Fisher Scientific, Pittsburgh, Pa.) supplemented with 100 μg/mL ampicillin (Fisher Scientific, Pittsburgh, Pa.) and grown overnight at 37° C. One liter of LB Miller supplemented with 100 μg/mL ampicillin in 2 L shaker flasks was incubated with 10 mL of overnight culture and grown at 37° C. until the culture reached an OD600~0.6-0.8 as measured by a BioPhotometer UV/VIS Photometer (Eppendorf, Westbury, N.Y.). IPTG (Isopropyl β-D-1-thiogalactopyranoside) was added to a final concentration of 0.5 mM, and grown for 4-6 hours at 30° C. Cells were harvested by centrifugation at 5,500×g for 10 minutes at 4° C. The cell pellet was frozen and stored at −80° C.

The cell pellet was thawed on ice and resuspended in lysis buffer (100 mM Tris-HCl pH 8.0, 500 mM NaCl, 1 mM EDTA pH 8.0) and lysed by sonication. Crude cell lysate was clarified by centrifugation at 15,000×g for 30 minutes at 4° C. The clarified cell lysate was boiled and cell debris was removed by centrifugation. Protein in the supernatant was precipitated in acid at pH 3.5 through addition of HCl by titration to protein solution on ice while stirring then centrifuged for an additional 15,000×g for 30 minutes at 4° C. Supernatant was dialyzed against buffer A (20 mM Tris-HCl, pH 8.0). After dialysis the solution was filtered through a 0.45 μm syringe (Corning, N.Y. 14831) before loading onto a 20 mL HiPrep Q HP 16/10 column (GE Healthcare, Piscataway, N.J.). The Q-HP column was washed with five column volumes of buffer A and protein eluted using a linear gradient to 100% in five column volumes of buffer B (20 mM Tris-HCl, 1M NaCl, pH 8.0). Protein eluted at around 50-70% buffer B; peak fractions were pooled. Pooled samples were concentrated approximately tenfold using Amicon Ultra-15 centrifugal filters. Approximately 5 ml of the concentrated sample was loaded onto a HiPrep 26/60 Sephacryl S-75 HR column equilibrated with filtration buffer (25 mM sodium phosphate, 100 mM NaCl, pH 7.5). Peak fractions were pooled from the gel filtration column and dialyzed against 5 mM Tris-HCl, pH 7.5, concentrated to 3 mg/ml. These were filtered through a 0.2 μm pore size filter (Corning, N.Y. 14831) and stored at 4° C.

Recombinantly expressed full-length α-syn with an N-terminal acetylation was prepared and purified in the following way based on a protocol by Der-Sarkissian et al[25].

The α-syn plasmid was co-expressed with a heterodimeric protein acetylation complex from S. pombe to acetylate the N-terminus (pACYC-DUET, chloramphenicol, T7 promoter)[48]. The two vectors were co-transformed into *E. coli* BL21 (DE3) using media containing both ampicillin and chloramphenicol. Cell cultures were grown in TB media containing ampicillin and chloramphenicol and induced to express α-syn with 0.5 mM IPTG overnight at 25° C. Cells were harvested by centrifugation, the cell pellet then resuspended in lysis buffer (100 mM Tris-HCl pH 8.0, 500 mM NaCl, 1 mM EDTA pH 8.0, and 1 mM phenylmethylsulfonyl fluoride) and cells lysed using an Emulsiflex homogenizer (Avestin). The lysate was boiled and debris removed by centrifugation. A protein fraction was also removed by precipitation at low pH on ice followed by centrifugation. The remaining supernatant was pH adjusted by titration and dialyzed against Buffer A (20 mM Tris-HCl, pH 8.0, 1 mM DTT, 1 mM EDTA, pH 8.0). The resulting protein solution was loaded onto a 5 mL Q-Sepharose FF column (GE Healthcare) equilibrated with Buffer A and eluted against a linear gradient of Buffer B (1M NaCl, 20 mM Tris-HCl, pH 8.0, 1 mM DTT, 1 mM EDTA, pH 8.0). Fractions containing α-syn were identified using SDS-PAGE, collected, concentrated and further purified by size exclusion (Sephacryl S-100 16/60, GE Healthcare) in 20 mM Tris pH 8.0, 100 mM NaCl, 1 mM DTT, 1 mM EDTA. Purity of fractions was assessed by SDS-PAGE.

Acetylated protein was characterized by LC-MS27,[49]. Expected average mass: 14460.1 Da for alpha-synuclein and 14502.1 for acetylated alpha-synuclein. Observed average mass: 14464.0 Da for alpha-synuclein and 14506.0 for acetylated alpha-synuclein. The shift of 4 Da between observed and expected average masses is due to instrumental error.

Inhibitor Synthesis

Inhibitors were commercially obtained from Genscript Inc. at greater than 98% purity and solubilized in 100% DMSO at 10 mM concentration. Solubilized inhibitors were filtered with 0.1 µM filter and stored at −20° C. in 20 µL aliquots until further use.

Thioflavin T Assays

Fibril formation assays were performed with 50 µM protein concentration in conditions identical to those used for aggregating proteins for seeding assay, but with the addition of ThT. All assays were carried out in black Nunc 96-well optical bottom plates (Thermo Scientific). Plates were agitated at 600 rpm in 3-mm rotation diameter in a Varioskan microplate reader (Thermo) at 37° C. Fluorescence measurements were recorded every 30 mins using $\lambda_{ex}$=444 nm, $\lambda_{cm}$=482 nm, with an integration time of 200 µs.

Aggregation Assays

Purified α-synuclein was dialyzed in 0.1 M sodium sulfate, 25 mM sodium phosphate and aggregated by shaking in Torrey Pine shakers at 50 µM at 37° C. at speed 9 for 5-6 days.

Extraction of Sarkosyl Insoluble Protein Filaments From PD Human Brain Tissues

Human frozen brain tissues were obtained from UCLA Brain Tumor Translational Resource (BTTR). Sarkosyl insoluble protein was extracted using previously described protocols. Briefly, frozen tissue was homogenized in ice cold PBS using a dounce homogenizer at 200 mg/mL. The homogenate was then diluted in buffer A (10 mM Tris 7.4, 800 mM NaCl, 1 mM EGTA, 10% Sucrose) to 50 mg/mL in total volume of 1 mL and centrifuged at 20,700 g for 20 min at 4° C. The supernatant was collected in an ultracentrifuge tube and pellet was resuspended in 0.5 mL buffer A followed by centrifugation at 20,700 g for 20 mins at 4° C. The supernatants pooled together. 150 µl 10% sarkosyl (w/v) in Millipore water was then added and incubated for 1 h at room temperature on flat rotating shaker at 700 rpm. The solution was then centrifuged at 100,000 g for 1 h at 4° C. using SW 55 Rotor (Beckman Coulter). The supernatanat was discarded and pellet was washed with 5 mL Buffer A and centrifuged at 100,000 g for 20 mins at 4° C. The pellet was resuspended in 100 µl 50 mM Tris Ph 7.4

HEK 293T Cell Culture

HEK293T cells that stably express YFP labeled WT α-syn and A53T α-syn were a generous gift from Dr. Marc Diamond. Cells were grown in Dulbecco's modified Eagle's medium (Gibco) supplemented with 10% fetal bovine serum (HyClone), 1% penicillin/streptomycin (Gibco), and 1% glutamax (Gibco) in a humidified incubator in 37° C., 5% $CO_2$.

Seeding in HEK293T Cells 10,000 cells in 90 µL media were plated in 96 well black wall plate (Cat #3660) and allowed to adhere overnight. α-syn was transfected at a final monomer concentration of 125 nM. Lipofectamine 2000 was diluted in OptiMEM media (2.5+17.5 µL) and incubated at room temperature for 5 mins. Protein aggregates were diluted in OptiMEM media (1:20) and sonicated in a water bath sonicator for 3 mins at low pulse. Diluted lipofectamine and protein samples were then mixed 1:1 and incubated at room temperature for 20 mins and thereafter 10 µL was added to each well. All samples are added in triplicates and experiments were repeated a minimum of two times. For co-transfection of α-syn fibrils with inhibitors, the fibrils and inhibitors were diluted in OptiMEM and incubated for 3 hours followed by sonication.

Measurement of Intracellular Puncta in Cells

Puncta formation and cell growth was measured using Celigo Imaging Cell Cytometer allowing for unbiased measurement. Wells were imaged using fluorescent GFP channel and confluence was measured using Celigo analysis software. Images of entire well were taken and particles counted by ImageJ by particle analysis. Same settings were used to analyze wells of one plate at all days. Total particles counted in each well were normalized against the confluence and reported as particles per well.

Fibril Formation and Detection

Purified α-syn in 50 mM Tris, 150 mM KCl pH 7.5 was shaken at a concentration of 500 µM at 37° C. in Torey Pine shaker. To form the fibrillar samples of SubNACore and NACore, lyophilized peptides were dissolved to a final concentration of 500 µM in 5 mM lithium hydroxide, 20 mM sodium phosphate pH 7.5 and 0.1 M NaCl All samples were shaken at 37° C. in a Torey Pine shaker for 72 hours. Freshly dissolved samples were prepared by dissolving lyophilized peptides immediately prior to addition to cells for assays.

Turbidity measurements were used to compare NACore and SubNACore aggregation. Peptide samples were freshly dissolved to 1.6 mM in a sample buffer with 5 mM LiOH and 1% DMSO and then filtered through a PVDF filter (Millipore, 0.1 µm). Measurements were performed using a black NUNC 96 well plate with 200 µL of sample/well (3-4 replicates per sample). The plate was agitated at 37° C., with a 3 mm rotation diameter, at 300 rpm in a Varioskan microplate reader (Thermo). Absorbance readings were recorded every 3-15 minutes at 340 nm.

Negative Stain Transmission Electron Microscopy

Cytotoxicity samples were evaluated for presence of fibrils by electron microscopy. Briefly, 5 µL samples were spotted directly on freshly glow-discharged carbon-coated electron microscopy grids (Ted Pella, Redding, Calif.). After 4 min incubation, grids were rinsed twice with 5-µL distilled water and stained with 2% uranyl acetate for 1 min. Specimens were examined on an FEI T12 electron microscope.

Fibril Diffraction

Fibrils formed from purified α-syn with and without N-terminal acetylation were concentrated by centrifugation, washed, and oriented while drying between two glass capillaries. Likewise, NACore nanocrystals were also concentrated, washed, and allowed to orient while drying between two glass capillaries. Aligned fibrils or nanocrystals were mounted onto a cryopin for diffraction using 1.54 Å x-rays produced by a Rigaku rotating anode generator equipped with an HTC imaging plate and a built in X-Stream cryo-cooling device. All patterns were collected at a distance of 180 mm and analyzed using the Adxv software package.

Cytotoxicity Assays

Adherent PC12 cells were cultured in ATCC-formulated RPMI 1640 medium (ATCC; cat. #30-2001) supplemented with 10% horse serum and 5% fetal bovine serum and plated at 10,000 per well to a final volume of 90 µl. All MTT assays were performed with Cell Titer 96 aqueous non-radioactive cell proliferation kit (MTT, Promega cat #4100). Cells were cultured in 96-well plates for 20 h at 37° C. in 5% CO2 prior to addition of samples (Costar cat. #3596). 10 µL of sample was added to each well containing 90 µL medium and incubated for 24 h at 37° C. in 5% CO2. Then, 15 µL dye solution (Promega cat #4102) was added into each well, followed by incubation for 4 h at 37° C. in 5% CO2. This was followed by the addition of 100 µl solubilization Solution/Stop Mix (Promega cat #4101) to each well. After 12 h incubation at room temperature, the absorbance was measured at 570 nm. Background absorbance was recorded at 700 nm. The data was normalized with cells treated with 1% (w/v) SDS to 0% reduction, and cells treated with sample buffer to 100% reduction.

Lactose dehydrogenase assays were done using CytoTox-ONE™ Homogeneous Membrane Integrity, (Promega, cat #G7890) as per manufacturers instructions. Briefly, cells were plated in 96 well black-wall, clear bottom (Fisher Cat #07-200-588) tissue culture plates at 10,000 cells per well to a final volume of 90 µL. Cells were incubated for an additional 20 h at 37° C. in 5% CO2 prior to addition of samples. Next, 10 µl of sample was added to each well following which the cells were incubated for another 24 hours. 100 µl of reagent was added to each well and incubated for 15 mins at room temperature. The addition of 50 µL of stop solution stopped the reaction. Fluorescence was measured using excitation and emission wavelengths of 560 nm and 590 nm, respectively. Data was normalized using cells treated with buffer as 0% release and 0.1% triton X-100 as 100% release.

The atomic coordinates of the structure of NACore: GAVVTGVTAVA (SEQ ID NO:46) below are in Table 3. The atomic coordinates of PreNAC below are in Table 4.

The atomic structure of NACore reveals an amyloid fibril formed from a self-complementary pair of β-sheets, tightly mating to form a steric zipper. By Rossetta-based computational modeling, each of the inhibitors was designed to bind to the tip of the steric zipper and thus 'cap' the fibrils, preventing further molecules of alpha-synuclein to add to the fibrils. We designed 3 candidate inhibitors; S37, S61 and S71 that bind favorably to one or both ends of the zipper. The computed binding energies and shape complementarity of each of the three inhibitors with the fibril are also favorable for binding. Each of the inhibitors retains most residues of the native sequence of NACore but also contain one or more modified residues. Rodriquez et al. showed that a smaller 9-residue segment within NACore [69-77] aggregates slower than NACore and the structure is similar to NACore. In order to prevent the self-aggregation of our designed inhibitors, we used the shorter segment along with one or more modifications. S37 has a W mutation at Thr72 and an additional poly-lysine tag at the C-terminus to induce charge-charge repulsion. It is predicted to bind both tips of the steric zipper fibril (i.e. top and bottom). S61 and S62 retain the same inhibitor sequence as S37 but instead of poly-lysine tag, a TAT tag is added to aid solubility and prevent self-aggregation. S71 has a methylated glycine at Gly73 that weakens hydrogen bonding along the β-sheet and an additional TAT tag for solubility and cell penetration.

Example II: Computational Design

Based on the atomic structure of a fiber forming segment of α-synuclein, we designed a series of inhibitors that inhibit aggregation. We designed peptidic inhibitors to specifically "cap" the growing aggregates of α-synuclein. Using the ZipperDB algorithm (Goldschmidt et al.[55]), the crystallizable amyloid-forming segments in the NAC domain were identified. This domain has been reported to be necessary and sufficient for aggregation and toxicity of α-synuclein (Bodles et al.[20]). The identified segments (α-synuclein segments comprised of residues 69-77 and residues 68-78) were chemically synthesized and crystallized; their three-dimensional structures were determined by micro-crystallography and micro-electron diffraction (MicroED). We then applied a Rosetta-based method (Sievers et al.[36]) in their steps to design inhibitors that disrupt α-synuclein aggregation, using the α-synuclein 69-77 structure or the α-synuclein 68-78 structure as a template. Putative inhibitors were identified and selected for experimental characterization.

Example III—Second Round of Design—Rational, Sequence-Based Design

In another round of design, we started from several alpha-synuclein amyloidogenic segments: 47-56, 68-78 and 84-94. N-methylation was introduced at two separate residues in the native amino acid sequence. In these N-methyl amino acids, an additional methyl group replaces the amine hydrogen. Thus it blocks the hydrogen bond and prevents the addition of peptide monomers on its growing end. In addition to N-methylation, additional polar/charged amino acid extensions from native alpha-synuclein sequence were considered to improve the overall solubility of the peptide inhibitor.

TABLE 3

TITLE ELECTRON DIFFRACTION STRUCTURE OF THE PARKINSON'S DISEASE TOXIC CORE
TITLE 2 OF ALPHA-SYNUCLEIN AMYLOID, GAVVTGVTAVA
COMPND MOL_ID: 1;
COMPND 2 MOLECULE: ALPHA-SYNUCLEIN;
COMPND 3 CHAIN: A;
COMPND 4 SYNONYM: NON-A BETA COMPONENT OF AD AMYLOID, NON-A4 COMPONENT OF

TABLE 3-continued

```
COMPND 5 AMYLOID PRECURSOR, NACP;
COMPND 6 ENGINEERED: YES
SOURCE MOL_ID: 1;
SOURCE 2 SYNTHETIC: YES;
SOURCE 3 ORGANISM_SCIENTIFIC: HOMO SAPIENS;
SOURCE 4 ORGANISM_COMMON: HUMAN;
SOURCE 5 ORGANISM_TAXID: 9606;
SOURCE 6 OTHER_DETAILS: SYNTHETIC PEPTIDE GAVVTGVTAVA CORRESPONDING TO
SOURCE 7 SEGMENT 68-78 OF HUMAN ALPHA-SYNUCLEIN
KEYWDS AMYLOID, ALPHA-SYNUCLEIN, PARKINSON'S DISEASE, TOXIC CORE, NACORE,
KEYWDS 2 LIPID BINDING PROTEIN
EXPDTA ELECTRON CRYSTALLOGRAPHY
AUTHOR J.A.RODRIGUEZ,M.IVANOVA,M.R.SAWAYA,D.CASCIO,F.REYES,D.SHI,L.JOHNSON,
AUTHOR 2 E.GUENTHER,S.SANGWAN,J.HATTNE,B.NANNENGA,A.S.BREWSTER,
AUTHOR 3 M.MESSERSCHMIDT,S.BOUTET,N.K.SAUTER,T.GONEN,D.S.EISENBERG
JRNL AUTH J.A.RODRIGUEZ,M.IVANOVA,M.R.SAWAYA,D.CASCIO,F.REYES,D.SHI,
JRNL AUTH 2 L.JOHNSON,E.GUENTHER,S.SANGWAN,J.HATTNE,B.NANNENGA,
JRNL AUTH 3 A.S.BREWSTER,M.MESSERSCHMIDT,S.BOUTET,N.K.SAUTER,T.GONEN,
JRNL AUTH 4 D.S.EISENBERG
JRNL TITL MICROED STRUCTURE OF THE TOXIC CORE OF ALPHA-SYNUCLEIN
JRNL TITL 2 AMYLOID, THE PROTEIN ASSOCIATED WITH THE DEVELOPMENT OF
JRNL TITL 3 PARKINSONS DISEASE
JRNL REF TO BE PUBLISHED
JRNL REFN
REMARK 2
REMARK 2 RESOLUTION. 1.43 ANGSTROMS.
REMARK 3
REMARK 3 REFINEMENT.
REMARK 3 PROGRAM : BUSTER
REMARK 3 AUTHORS : BRICOGNE,BLANC,BRANDL,FLENSBURG,KELLER,
REMARK 3 : PACIOREK,ROVERSI,SMART,VONRHEIN,WOMACK,
REMARK 3 : MATTHEWS,TEN EYCK,TRONRUD
REMARK 3
REMARK 3 DATA USED IN REFINEMENT.
REMARK 3 RESOLUTION RANGE HIGH (ANGSTROMS) : 1.43
REMARK 3 RESOLUTION RANGE LOW (ANGSTROMS) : 16.43
REMARK 3 DATA CUTOFF (SIGMA(F)) : 0.000
REMARK 3 COMPLETENESS FOR RANGE (%) : 87.9
REMARK 3 NUMBER OF REFLECTIONS : 1073
REMARK 3
REMARK 3 FIT TO DATA USED IN REFINEMENT.
REMARK 3 CROSS-VALIDATION METHOD : THROUGHOUT
REMARK 3 FREE R VALUE TEST SET SELECTION : RANDOM
REMARK 3 R VALUE (WORKING + TEST SET) : 0.251
REMARK 3 R VALUE (WORKING SET) : 0.248
REMARK 3 FREE R VALUE : 0.275
REMARK 3 FREE R VALUE TEST SET SIZE (%) : 11.840
REMARK 3 FREE R VALUE TEST SET COUNT : 127
REMARK 3 ESTIMATED ERROR OF FREE R VALUE : NULL
REMARK 3
REMARK 3 FIT IN THE HIGHEST RESOLUTION BIN.
REMARK 3 TOTAL NUMBER OF BINS USED : 5
REMARK 3 BIN RESOLUTION RANGE HIGH (ANGSTROMS) : 1.43
REMARK 3 BIN RESOLUTION RANGE LOW (ANGSTROMS) : 1.60
REMARK 3 BIN COMPLETENESS (WORKING+TEST) (%) : 87.88
REMARK 3 REFLECTIONS IN BIN (WORKING + TEST SET) : 286
REMARK 3 BIN R VALUE (WORKING + TEST SET) : 0.2642
1
REMARK 3 REFLECTIONS IN BIN (WORKING SET) : 245
REMARK 3 BIN R VALUE (WORKING SET) : 0.2532
REMARK 3 BIN FREE R VALUE : 0.3310
REMARK 3 BIN FREE R VALUE TEST SET SIZE (%) : 14.34
REMARK 3 BIN FREE R VALUE TEST SET COUNT : 41
REMARK 3 ESTIMATED ERROR OF BIN FREE R VALUE : NULL
REMARK 3
REMARK 3 NUMBER OF NON-HYDROGEN ATOMS USED IN REFINEMENT.
REMARK 3 PROTEIN ATOMS : 66
REMARK 3 NUCLEIC ACID ATOMS : 0
REMARK 3 HETEROGEN ATOMS : 0
REMARK 3 SOLVENT ATOMS : 2
REMARK 3
REMARK 3 B VALUES.
REMARK 3 FROM WILSON PLOT (A**2) : 10.33
REMARK 3 MEAN B VALUE (OVERALL, A**2) : 12.75
REMARK 3 OVERALL ANISOTROPIC B VALUE.
REMARK 3 B11 (A**2) : -3.98760
REMARK 3 B22 (A**2) : 3.49080
REMARK 3 B33 (A**2) : 0.49680
REMARK 3 B12 (A**2) : 0.00000
REMARK 3 B13 (A**2) : -1.55090
```

TABLE 3-continued

```
REMARK 3 B23 (A**2) : 0.00000
REMARK 3
REMARK 3 ESTIMATED COORDINATE ERROR.
REMARK 3 ESD FROM LUZZATI PLOT (A) : 0.305
REMARK 3 DPI (BLOW EQ-10) BASED ON R VALUE (A) : NULL
REMARK 3 DPI (BLOW EQ-9) BASED ON FREE R VALUE (A) : NULL
REMARK 3 DPI (CRUICKSHANK) BASED ON R VALUE (A) : 0.108
REMARK 3 DPI (CRUICKSHANK) BASED ON FREE R VALUE (A) : NULL
REMARK 3
REMARK 3 REFERENCES: BLOW, D. (2002) ACTA CRYST D58, 792-797
REMARK 3 CRUICKSHANK, D.W.J. (1999) ACTA CRYST D55, 583-601
REMARK 3
REMARK 3 CORRELATION COEFFICIENTS.
REMARK 3 CORRELATION COEFFICIENT FO-FC : 0.913
REMARK 3 CORRELATION COEFFICIENT FO-FC FREE : 0.900
REMARK 3
REMARK 3 NUMBER OF GEOMETRIC FUNCTION TERMS DEFINED : 15
REMARK 3 TERM COUNT WEIGHT FUNCTION.
REMARK 3 BOND LENGTHS : 65 ; 2.000 ; HARMONIC
REMARK 3 BOND ANGLES : 90 ; 2.000 ; HARMONIC
REMARK 3 TORSION ANGLES : 16 ; 2.000 ; SINUSOIDAL
REMARK 3 TRIGONAL CARBON PLANES : 1 ; 2.000 ; HARMONIC
REMARK 3 GENERAL PLANES : 10 ; 5.000 ; HARMONIC
REMARK 3 ISOTROPIC THERMAL FACTORS : 65 ; 20.000 ; HARMONIC
REMARK 3 BAD NON-BONDED CONTACTS : NULL ; NULL ; NULL
REMARK 3 IMPROPER TORSIONS : NULL ; NULL ; NULL
REMARK 3 PSEUDOROTATION ANGLES : NULL ; NULL ; NULL
REMARK 3 CHIRAL IMPROPER TORSION : 11 ; 5.000 ; SEMIHARMONIC
REMARK 3 SUM OF OCCUPANCIES : NULL ; NULL ; NULL
REMARK 3 UTILITY DISTANCES : NULL ; NULL ; NULL
REMARK 3 UTILITY ANGLES : NULL ; NULL ; NULL
REMARK 3 UTILITY TORSION : NULL ; NULL ; NULL
REMARK 3 IDEAL-DIST CONTACT TERM : 76 ; 4.000 ; SEMIHARMONIC
REMARK 3
REMARK 3 RMS DEVIATIONS FROM IDEAL VALUES.
REMARK 3 BOND LENGTHS (A) : 0.010
REMARK 3 BOND ANGLES (DEGREES) : 1.65
REMARK 3 PEPTIDE OMEGA TORSION ANGLES (DEGREES) : 4.08
REMARK 3 OTHER TORSION ANGLES (DEGREES) : 6.49
REMARK 3
REMARK 3 TLS DETAILS
REMARK 3 NUMBER OF TLS GROUPS : NULL
2
REMARK 3
REMARK 3 OTHER REFINEMENT REMARKS: NULL
REMARK 4
REMARK 4 4RIL COMPLIES WITH FORMAT V. 3.30, 13-JUL-11
REMARK 100
REMARK 100 THIS ENTRY HAS BEEN PROCESSED BY RCSB ON 09-OCT-14.
REMARK 100 THE RCSB ID CODE IS RCSB087390.
REMARK 240
REMARK 240 EXPERIMENTAL DETAILS
REMARK 240 RECONSTRUCTION METHOD : NULL
REMARK 240 SAMPLE TYPE : NULL
REMARK 240 SPECIMEN TYPE : NULL
REMARK 240 DATA ACQUISITION
REMARK 240 DATE OF DATA COLLECTION : 28-AUG-14
REMARK 240 TEMPERATURE (KELVIN) : 100.0
REMARK 240 PH : NULL
REMARK 240 NUMBER OF CRYSTALS USED : 4
REMARK 240 MICROSCOPE MODEL : TECNAI F20 TEM
REMARK 240 DETECTOR TYPE : TVIPS F416 CMOS CAMERA
REMARK 240 ACCELERATION VOLTAGE (KV) : NULL
REMARK 240 NUMBER OF UNIQUE REFLECTIONS : 1073
REMARK 240 RESOLUTION RANGE HIGH (A) : 1.430
REMARK 240 RESOLUTION RANGE LOW (A) : 16.430
REMARK 240 DATA SCALING SOFTWARE : XSCALE
REMARK 240 COMPLETENESS FOR RANGE (%) : 89.9
REMARK 240 DATA REDUNDANCY : 4.400
REMARK 240 IN THE HIGHEST RESOLUTION SHELL
REMARK 240 HIGHEST RESOLUTION SHELL, RANGE HIGH (A) :1.43
REMARK 240 HIGHEST RESOLUTION SHELL, RANGE LOW (A) :1.60
REMARK 240 COMPLETENESS FOR SHELL (%) : 82.5
REMARK 240 DATA REDUNDANCY IN SHELL : 4.40
REMARK 240 R MERGE FOR SHELL (I) : 0.56500
REMARK 240 METHOD USED TO DETERMINE THE STRUCTURE: MOLECULAR REPLACEMENT
REMARK 240 SOFTWARE USED : PHASER
REMARK 240 STARTING MODEL : 4RIK
REMARK 290
REMARK 290 CRYSTALLOGRAPHIC SYMMETRY
```

TABLE 3-continued

```
REMARK 290 SYMMETRY OPERATORS FOR SPACE GROUP: C 1 2 1
REMARK 290
REMARK 290       SYMOP   SYMMETRY
REMARK 290      NNNMMM   OPERATOR
REMARK 290        1555   X,Y,Z
REMARK 290        2555   -X,Y,-Z
REMARK 290        3555   X+1/2,Y+1/2,Z
REMARK 290        4555   -X+1/2,Y+1/2,-Z
REMARK 290
REMARK 290     WHERE NNN -> OPERATOR NUMBER
REMARK 290           MMM -> TRANSLATION VECTOR
REMARK 290
REMARK 290   CRYSTALLOGRAPHIC SYMMETRY TRANSFORMATIONS
REMARK 290   THE FOLLOWING TRANSFORMATIONS OPERATE ON THE ATOM/HETATM
REMARK 290   RECORDS IN THIS ENTRY TO PRODUCE CRYSTALLOGRAPHICALLY
REMARK 290   RELATED MOLECULES.
REMARK 290     SMTRY1   1  1.000000  0.000000  0.000000        0.00000
REMARK 290     SMTRY2   1  0.000000  1.000000  0.000000        0.00000
REMARK 290     SMTRY3   1  0.000000  0.000000  1.000000        0.00000
REMARK 290     SMTRY1   2 -1.000000  0.000000  0.000000        0.00000
REMARK 290     SMTRY2   2  0.000000  1.000000  0.000000        0.00000
REMARK 290     SMTRY3   2  0.000000  0.000000 -1.000000        0.00000
REMARK 290     SMTRY1   3  1.000000  0.000000  0.000000       35.40500
REMARK 290     SMTRY2   3  0.000000  1.000000  0.000000        2.41000
REMARK 290     SMTRY3   3  0.000000  0.000000  1.000000        0.00000
REMARK 290     SMTRY1   4 -1.000000  0.000000  0.000000       35.40500
REMARK 290     SMTRY2   4  0.000000  1.000000  0.000000        2.41000
3
REMARK 290     SMTRY3   4  0.000000  0.000000 -1.000000        0.00000
REMARK 290
REMARK 290 REMARK: NULL
REMARK 300
REMARK 300 BIOMOLECULE: 1, 2
REMARK 300 SEE REMARK 350 FOR THE AUTHOR PROVIDED AND/OR PROGRAM
REMARK 300 GENERATED ASSEMBLY INFORMATION FOR THE STRUCTURE IN
REMARK 300 THIS ENTRY. THE REMARK MAY ALSO PROVIDE INFORMATION ON
REMARK 300 BURIED SURFACE AREA.
REMARK 300 REMARK: THE BIOLOGICAL UNIT IS A PAIR OF BETA-SHEETS. ONE SHEET IS
REMARK 300 COMPOSED OF CHAIN A AND UNIT CELL TRANSLATIONS ALONG THE B
REMARK 300 DIMENSION. THE OTHER SHEET IS COMPOSED OF THE SYMMETRY MATE -X+1/2,
REMARK 300 Y+1/2,-Z, AND UNIT CELL TRANSLATIONS ALONG B.
REMARK 350
REMARK 350 COORDINATES FOR A COMPLETE MULTIMER REPRESENTING THE KNOWN
REMARK 350 BIOLOGICALLY SIGNIFICANT OLIGOMERIZATION STATE OF THE
REMARK 350 MOLECULE CAN BE GENERATED BY APPLYING BIOMT TRANSFORMATIONS
REMARK 350 GIVEN BELOW. BOTH NON-CRYSTALLOGRAPHIC AND
REMARK 350 CRYSTALLOGRAPHIC OPERATIONS ARE GIVEN.
REMARK 350
REMARK 350 BIOMOLECULE: 1
REMARK 350 AUTHOR DETERMINED BIOLOGICAL UNIT: TETRAMERIC
REMARK 350 APPLY THE FOLLOWING TO CHAINS: A
REMARK 350   BIOMT1   1  1.000000  0.000000  0.000000        0.00000
REMARK 350   BIOMT2   1  0.000000  1.000000  0.000000        0.00000
REMARK 350   BIOMT3   1  0.000000  0.000000  1.000000        0.00000
REMARK 350   BIOMT1   2  1.000000  0.000000  0.000000        0.00000
REMARK 350   BIOMT2   2  0.000000  1.000000  0.000000        4.82000
REMARK 350   BIOMT3   2  0.000000  0.000000  1.000000        0.00000
REMARK 350   BIOMT1   3 -1.000000  0.000000  0.000000       35.40500
REMARK 350   BIOMT2   3  0.000000  1.000000  0.000000        2.41000
REMARK 350   BIOMT3   3  0.000000  0.000000 -1.000000        0.00000
REMARK 350   BIOMT1   4 -1.000000  0.000000  0.000000       35.40500
REMARK 350   BIOMT2   4  0.000000  1.000000  0.000000        7.23000
REMARK 350   BIOMT3   4  0.000000  0.000000 -1.000000        0.00000
REMARK 350
REMARK 350 BIOMOLECULE: 2
REMARK 350 AUTHOR DETERMINED BIOLOGICAL UNIT: MONOMERIC
REMARK 350 APPLY THE FOLLOWING TO CHAINS: A
REMARK 350   BIOMT1   1  1.000000  0.000000  0.000000        0.00000
REMARK 350   BIOMT2   1  0.000000  1.000000  0.000000        0.00000
REMARK 350   BIOMT3   1  0.000000  0.000000  1.000000        0.00000
DBREF 4RIL A 1 11 UNP P37840 SYUA_HUMAN 68 78
SEQRES 1 A 11 GLY ALA VAL VAL THR GLY VAL THR ALA VAL ALA
FORMUL 2 HOH *2(H2 O)
CRYST1 70.810 4.820 16.790 90.00 105.68 90.00 C 1 2 1 4
ORIGX1 1.000000 0.000000 0.000000    0.00000
ORIGX2 0.000000 1.000000 0.000000    0.00000
ORIGX3 0.000000 0.000000 1.000000    0.00000
SCALE1 0.014122 0.000000 0.003964    0.00000
SCALE2 0.000000 0.207469 0.000000    0.00000
SCALE3 0.000000 0.000000 0.061861    0.00000
```

TABLE 3-continued

```
ATOM 1 N GLY A 1 -1.664 2.302 6.349 1.00 23.58 N
ATOM 2 CA GLY A 1 -1.194 2.605 5.007 1.00 23.02 C
ATOM 3 C GLY A 1 0.105 1.901 4.702 1.00 21.89 C
ATOM 4 O GLY A 1 0.121 0.676 4.579 1.00 20.14 O
ATOM 5 N ALA A 2 1.197 2.666 4.558 1.00 16.28 N
ATOM 6 CA ALA A 2 2.509 2.094 4.221 1.00 15.41 C
ATOM 7 C ALA A 2 3.664 2.731 5.005 1.00 12.05 C
ATOM 8 O ALA A 2 3.668 3.942 5.227 1.00 10.77 O
ATOM 9 CB ALA A 2 2.764 2.186 2.712 1.00 15.67 C
ATOM 10 N VAL A 3 4.640 1.905 5.417 1.00 5.98 N
ATOM 11 CA VAL A 3 5.852 2.304 6.129 1.00 3.93 C
ATOM 12 C VAL A 3 7.023 1.700 5.344 1.00 5.93 C
ATOM 13 O VAL A 3 7.217 0.485 5.388 1.00 6.66 O
ATOM 14 CB VAL A 3 5.856 1.891 7.629 1.00 7.66 C
ATOM 15 CG1 VAL A 3 7.148 2.337 8.330 1.00 6.70 C
ATOM 16 CG2 VAL A 3 4.661 2.494 8.333 1.00 6.73 C
ATOM 17 N VAL A 4 7.702 2.522 4.533 1.00 3.26 N
ATOM 18 CA VAL A 4 8.782 2.087 3.638 1.00 4.61 C
ATOM 19 C VAL A 4 10.065 2.743 4.088 1.00 4.32 C
ATOM 20 O VAL A 4 10.149 3.973 4.071 1.00 3.00 O
ATOM 21 CB VAL A 4 8.458 2.457 2.171 1.00 8.53 C
ATOM 22 CG1 VAL A 4 9.486 1.874 1.188 1.00 9.58 C
ATOM 23 CG2 VAL A 4 7.041 2.046 1.790 1.00 9.20 C
ATOM 24 N THR A 5 11.066 1.952 4.438 1.00 3.32 N
ATOM 25 CA THR A 5 12.360 2.426 4.896 1.00 3.88 C
ATOM 26 C THR A 5 13.504 1.769 4.092 1.00 5.43 C
ATOM 27 O THR A 5 13.567 0.539 4.039 1.00 6.20 O
ATOM 28 CB THR A 5 12.540 2.051 6.351 1.00 6.84 C
ATOM 29 OG1 THR A 5 11.414 2.503 7.130 1.00 9.13 O
ATOM 30 CG2 THR A 5 13.891 2.524 6.943 1.00 10.98 C
ATOM 31 N GLY A 6 14.417 2.588 3.546 1.00 6.04 N
ATOM 32 CA GLY A 6 15.571 2.100 2.793 1.00 6.46 C
ATOM 33 C GLY A 6 16.874 2.688 3.292 1.00 7.38 C
ATOM 34 O GLY A 6 16.959 3.896 3.501 1.00 6.32 O
ATOM 35 N VAL A 7 17.913 1.864 3.436 1.00 4.11 N
ATOM 36 CA VAL A 7 19.223 2.311 3.884 1.00 5.04 C
ATOM 37 C VAL A 7 20.243 1.730 2.870 1.00 4.68 C
ATOM 38 O VAL A 7 20.244 0.519 2.678 1.00 5.69 O
ATOM 39 CB VAL A 7 19.532 1.802 5.294 1.00 9.15 C
ATOM 40 CG1 VAL A 7 21.007 1.991 5.629 1.00 9.39 C
ATOM 41 CG2 VAL A 7 18.606 2.431 6.367 1.00 9.75 C
ATOM 42 N THR A 8 21.105 2.570 2.279 1.00 3.68 N
ATOM 43 CA THR A 8 22.201 2.169 1.357 1.00 4.35 C
ATOM 44 C THR A 8 23.468 2.783 1.930 1.00 6.01 C
ATOM 45 O THR A 8 23.530 4.005 2.031 1.00 6.48 O
ATOM 46 CB THR A 8 21.874 2.496 -0.083 1.00 12.43 C
ATOM 47 OG1 THR A 8 20.601 1.921 -0.394 1.00 14.76 O
ATOM 48 CG2 THR A 8 22.929 1.954 -1.075 1.00 13.32 C
ATOM 49 N ALA A 9 24.453 1.977 2.339 1.00 7.04 N
ATOM 50 CA ALA A 9 25.628 2.542 2.994 1.00 9.57 C
ATOM 51 C ALA A 9 26.967 1.849 2.849 1.00 11.59 C
ATOM 52 O ALA A 9 27.052 0.628 2.756 1.00 8.18 O
ATOM 53 CB ALA A 9 25.328 2.729 4.478 1.00 10.30 C
ATOM 54 N VAL A 10 28.017 2.646 2.956 1.00 10.58 N
ATOM 55 CA VAL A 10 29.405 2.206 3.043 1.00 12.39 C
ATOM 56 C VAL A 10 29.896 2.880 4.314 1.00 18.51 C
ATOM 57 O VAL A 10 30.171 4.075 4.301 1.00 16.08 O
ATOM 58 CB VAL A 10 30.273 2.561 1.816 1.00 17.83 C
ATOM 59 CG1 VAL A 10 31.744 2.243 2.085 1.00 18.89 C
ATOM 60 CG2 VAL A 10 29.778 1.831 0.567 1.00 17.39 C
ATOM 61 N ALA A 11 29.916 2.136 5.427 1.00 17.81 N
ATOM 62 CA ALA A 11 30.340 2.647 6.726 1.00 23.47 C
ATOM 63 C ALA A 11 31.643 1.988 7.097 1.00 51.68 C
ATOM 64 O ALA A 11 31.622 0.916 7.734 1.00 58.63 O
ATOM 65 CB ALA A 11 29.289 2.350 7.778 1.00 24.49 C
ATOM 66 OXT ALA A 11 32.691 2.485 6.653 1.00 74.50 O
TER 67 ALA A 11
HETATM 68 O HOH A 101 9.830 4.990 7.085 1.00 11.92 O
HETATM 69 O HOH A 102 18.548 3.873 0.260 1.00 20.36 O
MASTER 203 0 0 0 0 0 0 6 68 1 0 1
END
```

The atomic coordinates of the structure of PreNAC: GVVHGVTTVA (SEQ ID NO:47) below in Table 4

TABLE 4

HEADER ---- 27-APR-15 xxxx
COMPND ---
REMARK 3
REMARK 3 REFINEMENT.
REMARK 3 PROGRAM : REFMAC 5.8.0073
REMARK 3 AUTHORS : MURSHUDOV,SKUBAK,LEBEDEV,PANNU,
REMARK 3 STEINER,NICHOLLS,WINN,LONG,VAGIN
REMARK 3
REMARK 3 REFINEMENT TARGET : MAXIMUM LIKELIHOOD
REMARK 3
REMARK 3 DATA USED IN REFINEMENT.
REMARK 3 RESOLUTION RANGE HIGH (ANGSTROMS) : 1.41
REMARK 3 RESOLUTION RANGE LOW (ANGSTROMS) : 32.94
REMARK 3 DATA CUTOFF (SIGMA(F)) : NONE
REMARK 3 COMPLETENESS FOR RANGE (%) : 86.73
REMARK 3 NUMBER OF REFLECTIONS : 1006
REMARK 3
REMARK 3 FIT TO DATA USED IN REFINEMENT.
REMARK 3 CROSS-VALIDATION METHOD : THROUGHOUT
REMARK 3 FREE R VALUE TEST SET SELECTION : RANDOM
REMARK 3 R VALUE (WORKING + TEST SET) : 0.26104
REMARK 3 R VALUE (WORKING SET) : 0.25243
REMARK 3 FREE R VALUE : 0.33523
REMARK 3 FREE R VALUE TEST SET SIZE (%) : 10.0
REMARK 3 FREE R VALUE TEST SET COUNT : 112
REMARK 3
REMARK 3 FIT IN THE HIGHEST RESOLUTION BIN.
REMARK 3 TOTAL NUMBER OF BINS USED : 20
REMARK 3 BIN RESOLUTION RANGE HIGH : 1.409
REMARK 3 BIN RESOLUTION RANGE LOW : 1.446
REMARK 3 REFLECTION IN BIN (WORKING SET) : 49
REMARK 3 BIN COMPLETENESS (WORKING+TEST) (%) : 51.43
REMARK 3 BIN R VALUE (WORKING SET) : 0.388
REMARK 3 BIN FREE R VALUE SET COUNT : 5
REMARK 3 BIN FREE R VALUE : 0.528
REMARK 3
REMARK 3 NUMBER OF NON-HYDROGEN ATOMS USED IN REFINEMENT.
REMARK 3 ALL ATOMS : 68
REMARK 3
REMARK 3 B VALUES.
REMARK 3 FROM WILSON PLOT (A**2) : NULL
REMARK 3 MEAN B VALUE (OVERALL, A**2) : 19.367
REMARK 3 OVERALL ANISOTROPIC B VALUE.
REMARK 3 B11 (A**2) : -0.23
REMARK 3 B22 (A**2) : -0.23
REMARK 3 B33 (A**2) : 0.49
REMARK 3 B12 (A**2) : 0.00
REMARK 3 B13 (A**2) : -0.30
REMARK 3 B23 (A**2) : -0.00
REMARK 3
REMARK 3 ESTIMATED OVERALL COORDINATE ERROR.
REMARK 3 ESU BASED ON R VALUE (A): 0.118
REMARK 3 ESU BASED ON FREE R VALUE (A): 0.133
REMARK 3 ESU BASED ON MAXIMUM LIKELIHOOD (A): 0.155
REMARK 3 ESU FOR B VALUES BASED ON MAXIMUM LIKELIHOOD (A**2): 4.934
REMARK 3
REMARK 3 CORRELATION COEFFICIENTS.
REMARK 3 CORRELATION COEFFICIENT FO-FC : 0.950
REMARK 3 CORRELATION COEFFICIENT FO-FC FREE : 0.895
REMARK 3
REMARK 3 RMS DEVIATIONS FROM IDEAL VALUES COUNT RMS WEIGHT
REMARK 3 BOND LENGTHS REFINED ATOMS (A): 66 ; 0.017 ; 0.019
REMARK 3 BOND LENGTHS OTHERS (A): 69 ; 0.010 ; 0.020
REMARK 3 BOND ANGLES REFINED ATOMS (DEGREES): 91 ; 1.876 ; 1.905
1
REMARK 3 BOND ANGLES OTHERS (DEGREES): 155 ; 0.648 ; 3.000
REMARK 3 TORSION ANGLES, PERIOD 1 (DEGREES): 9 ; 5.684 ; 5.000
REMARK 3 TORSION ANGLES, PERIOD 2 (DEGREES): 1 ;75.981 ;20.000
REMARK 3 TORSION ANGLES, PERIOD 3 (DEGREES): 7 ; 7.001 ;15.000
REMARK 3 CHIRAL-CENTER RESTRAINTS (A**3): 14 ; 0.098 ; 0.200
REMARK 3 GENERAL PLANES REFINED ATOMS (A): 73 ; 0.005 ; 0.020
REMARK 3 GENERAL PLANES OTHERS (A): 13 ; 0.001 ; 0.020
REMARK 3
REMARK 3 ISOTROPIC THERMAL FACTOR RESTRAINTS. COUNT RMS WEIGHT
REMARK 3 MAIN-CHAIN BOND REFINED ATOMS (A**2): 39 ; 6.545 ; 1.715
REMARK 3 MAIN-CHAIN BOND OTHER ATOMS (A**2): 38 ; 3.948 ; 1.607

TABLE 4-continued

```
REMARK 3 MAIN-CHAIN ANGLE REFINED ATOMS (A**2): 41 ; 8.395 ; 2.554
REMARK 3 MAIN-CHAIN ANGLE OTHER ATOMS (A**2) : 42 ; 8.555 ; 2.605
REMARK 3 SIDE-CHAIN BOND REFINED ATOMS (A**2): 27 ; 5.989 ; 2.165
REMARK 3 SIDE-CHAIN BOND OTHER ATOMS (A**2) : 27 ; 5.243 ; 2.077
REMARK 3 SIDE-CHAIN ANGLE OTHER ATOMS (A**2) : 44 ; 8.091 ; 3.056
REMARK 3 LONG RANGE B REFINED ATOMS (A**2) : 54 ; 9.624 ;14.765
REMARK 3 LONG RANGE B OTHER ATOMS (A**2) : 55 ;11.399 ;15.221
REMARK 3
REMARK 3 NCS RESTRAINTS STATISTICS
REMARK 3 NUMBER OF NCS GROUPS : NULL
REMARK 3
REMARK 3 TWIN DETAILS
REMARK 3 NUMBER OF TWIN DOMAINS : NULL
REMARK 3
REMARK 3
REMARK 3 TLS DETAILS
REMARK 3 NUMBER OF TLS GROUPS : NULL
REMARK 3
REMARK 3
REMARK 3 BULK SOLVENT MODELLING.
REMARK 3 METHOD USED : MASK
REMARK 3 PARAMETERS FOR MASK CALCULATION
REMARK 3 VDW PROBE RADIUS : 1.20
REMARK 3 ION PROBE RADIUS : 0.80
REMARK 3 SHRINKAGE RADIUS : 0.80
REMARK 3
REMARK 3 OTHER REFINEMENT REMARKS:
REMARK 3 HYDROGENS HAVE BEEN ADDED IN THE RIDING POSITIONS
REMARK 3 U VALUES : REFINED INDIVIDUALLY
REMARK 3
CRYST1 17.930 4.710 33.030 90.00 94.33 90.00 P 1 21 1
SCALE1 0.055772 0.000000 0.004219 0.00000
SCALE2 -0.000000 0.212314 0.000000 0.00000
SCALE3 0.000000 -0.000000 0.030362 0.00000
ATOM 1 N GLY A 47 -7.911 -0.639 18.278 1.00 20.19 N
ATOM 2 CA GLY A 47 -6.901 0.239 18.839 1.00 16.21 C
ATOM 3 C GLY A 47 -5.632 -0.528 19.111 1.00 16.40 C
ATOM 4 O GLY A 47 -5.600 -1.727 19.011 1.00 22.51 O
ATOM 5 N VAL A 48 -4.568 0.169 19.444 1.00 17.59 N
ATOM 6 CA VAL A 48 -3.313 -0.460 19.729 1.00 15.77 C
ATOM 7 CB VAL A 48 -2.269 -0.088 18.637 1.00 17.32 C
ATOM 8 CG1 VAL A 48 -0.855 -0.462 19.056 1.00 17.64 C
ATOM 9 CG2 VAL A 48 -2.659 -0.731 17.326 1.00 18.74 C
ATOM 10 C VAL A 48 -2.906 0.080 21.062 1.00 13.82 C
ATOM 11 O VAL A 48 -3.040 1.262 21.327 1.00 18.65 O
ATOM 12 N VAL A 49 -2.365 -0.782 21.895 1.00 16.57 N
ATOM 13 CA VAL A 49 -1.779 -0.342 23.136 1.00 16.11 C
ATOM 14 CB VAL A 49 -2.592 -0.887 24.317 1.00 16.48 C
ATOM 15 CG1 VAL A 49 -1.861 -0.622 25.628 1.00 20.39 C
ATOM 16 CG2 VAL A 49 -4.002 -0.324 24.303 1.00 20.73 C
ATOM 17 C VAL A 49 -0.366 -0.882 23.250 1.00 13.58 C
ATOM 18 O VAL A 49 -0.178 -2.043 23.137 1.00 20.25 O
ATOM 19 N HIS A 50 0.614 -0.063 23.557 1.00 16.22 N
2
ATOM 20 CA HIS A 50 2.002 -0.524 23.593 1.00 15.91 C
ATOM 21 CB HIS A 50 2.612 -0.176 22.220 1.00 18.19 C
ATOM 22 CG HIS A 50 4.036 -0.543 22.024 1.00 23.24 C
ATOM 23 ND1 HIS A 50 4.728 -1.390 22.851 1.00 32.41 N
ATOM 24 CE1 HIS A 50 5.964 -1.539 22.399 1.00 29.90 C
ATOM 25 NE2 HIS A 50 6.088 -0.839 21.291 1.00 34.03 N
ATOM 26 CD2 HIS A 50 4.892 -0.215 21.028 1.00 33.27 C
ATOM 27 C HIS A 50 2.680 0.171 24.736 1.00 14.51 C
ATOM 28 O HIS A 50 2.686 1.396 24.776 1.00 21.97 O
ATOM 29 N GLY A 51 3.213 -0.580 25.689 1.00 15.69 N
ATOM 30 CA GLY A 51 3.877 0.021 26.829 1.00 11.67 C
ATOM 31 C GLY A 51 2.957 0.800 27.740 1.00 12.93 C
ATOM 32 O GLY A 51 2.967 2.022 27.786 1.00 20.51 O
ATOM 33 N VAL A 52 2.174 0.081 28.498 1.00 15.10 N
ATOM 34 CA VAL A 52 1.315 0.692 29.514 1.00 14.31 C
ATOM 35 CB VAL A 52 -0.162 0.399 29.278 1.00 14.02 C
ATOM 36 CG1 VAL A 52 -1.002 0.803 30.489 1.00 16.11 C
ATOM 37 CG2 VAL A 52 -0.626 1.146 28.077 1.00 15.58 C
ATOM 38 C VAL A 52 1.778 0.094 30.802 1.00 13.92 C
ATOM 39 O VAL A 52 1.742 -1.133 30.969 1.00 20.14 O
ATOM 40 N THR A 53 2.253 0.954 31.698 1.00 17.96 N
ATOM 41 CA THR A 53 2.886 0.481 32.943 1.00 18.30 C
ATOM 42 CB THR A 53 4.381 0.885 33.010 1.00 20.92 C
ATOM 43 OG1 THR A 53 5.064 0.409 31.840 1.00 29.94 O
ATOM 44 CG2 THR A 53 5.063 0.255 34.175 1.00 22.40 C
ATOM 45 C THR A 53 2.116 1.037 34.132 1.00 14.85 C
```

TABLE 4-continued

```
ATOM  46 O   THR A 53  1.778  2.193 34.103 1.00 21.57 O
ATOM  47 N   THR A 54  1.840  0.202 35.151 1.00 15.66 N
ATOM  48 CA  THR A 54  1.239  0.607 36.427 1.00 14.08 C
ATOM  49 CB  THR A 54 -0.184  0.059 36.602 1.00 18.69 C
ATOM  50 OG1 THR A 54 -1.031  0.491 35.534 1.00 35.75 O
ATOM  51 CG2 THR A 54 -0.768  0.525 37.872 1.00 23.36 C
ATOM  52 C   THR A 54  2.061 -0.047 37.500 1.00 12.83 C
ATOM  53 O   THR A 54  2.023 -1.258 37.626 1.00 22.40 O
ATOM  54 N   VAL A 55  2.821  0.725 38.262 1.00 14.38 N
ATOM  55 CA  VAL A 55  3.639  0.203 39.339 1.00 13.58 C
ATOM  56 CB  VAL A 55  5.099  0.641 39.138 1.00 15.65 C
ATOM  57 CG1 VAL A 55  5.915  0.347 40.358 1.00 16.16 C
ATOM  58 CG2 VAL A 55  5.696 -0.078 37.939 1.00 17.66 C
ATOM  59 C   VAL A 55  3.100  0.756 40.673 1.00 14.57 C
ATOM  60 O   VAL A 55  2.916  1.968 40.780 1.00 16.23 O
ATOM  61 N   ALA A 56  2.809 -0.130 41.639 1.00 17.51 N
ATOM  62 CA  ALA A 56  2.466  0.268 43.022 1.00 26.29 C
ATOM  63 CB  ALA A 56  1.113 -0.279 43.465 1.00 21.51 C
ATOM  64 C   ALA A 56  3.547 -0.222 43.971 1.00 38.92 C
ATOM  65 O   ALA A 56  3.757 -1.425 44.111 1.00 69.25 O
ATOM  66 OXT ALA A 56  4.249  0.549 44.634 1.00 54.03 O
HETATM 67 O  HOH B 1   4.715  2.482 29.991 1.00 27.67 O
HETATM 68 O  HOH B 2  -1.034  3.065 33.500 1.00 32.66 O3
```

REFERENCES

1. Biere, A. L. et al. Parkinson's disease-associated alpha-synuclein is more fibrillogenic than beta- and gamma-synuclein and cannot cross-seed its homologs. J. Biol. Chem. 275, 34574-34579 (2000).
2. Giasson, B. I., Murray, I. V. J., Trojanowski, J. Q. & Lee, V. M.-Y. A Hydrophobic Stretch of 12 Amino Acid Residues in the Middle of α-Synuclein Is Essential for Filament Assembly. J. Biol. Chem. 276, 2380-2386 (2001).
3. Du, H.-N. et al. A peptide motif consisting of glycine, alanine, and valine is required for the fibrillization and cytotoxicity of human alpha-synuclein. Biochemistry (Mosc.) 42, 8870-8878 (2003).
4. Periquet, M., Fulga, T., Myllykangas, L., Schlossmacher, M. G. & Feany, M. B. Aggregated α-Synuclein Mediates Dopaminergic Neurotoxicity In Vivo. J. Neurosci. 27, 3338-3346 (2007).
5. Nannenga, B. L., Shi, D., Leslie, A. G. W. & Gonen, T. High-resolution structure determination by continuous-rotation data collection in MicroED. Nat. Methods 11, 927-930 (2014).
6. Shi, D., Nannenga, B. L., Iadanza, M. G. & Gonen, T. Three-dimensional electron crystallography of protein microcrystals. eLife 2, e01345 (2013).
7. Spillantini, M. G. et al. Alpha-synuclein in Lewy bodies. Nature 388, 839-840 (1997).
8. Goedert, M., Spillantini, M. G., Del Tredici, K. & Braak, H. 100 years of Lewy pathology. Nat. Rev. Neurol. 9, 13-24 (2013).
9. Polymeropoulos, M. H. et al. Mutation in the alpha-synuclein gene identified in families with Parkinson's disease. Science 276, 2045-2047 (1997).
10. Krüger, R. et al. Ala30Pro mutation in the gene encoding alpha-synuclein in Parkinson's disease. Nat. Genet. 18, 106-108 (1998).
11. Zarranz, J. J. et al. The new mutation, E46K, of alpha-synuclein causes Parkinson and Lewy body dementia. Ann. Neurol. 55, 164-173 (2004).
12. Ibáñez, P. et al. Causal relation between alpha-synuclein gene duplication and familial Parkinson's disease. Lancet 364, 1169-1171 (2004).
13. Singleton, A. B. et al. alpha-Synuclein locus triplication causes Parkinson's disease. Science 302, 841 (2003).
14. Uéda, K. et al. Molecular cloning of cDNA encoding an unrecognized component of amyloid in Alzheimer disease. Proc. Natl. Acad. Sci. U.S.A. 90, 11282-11286 (1993).
15. Han, H., Weinreb, P. H. & Lansbury, P. T. The core Alzheimer's peptide NAC forms amyloid fibrils which seed and are seeded by beta-amyloid: is NAC a common trigger or target in neurodegenerative disease? Chem. Biol. 2, 163-169 (1995).
16. El-Agnaf, O. M. et al. Aggregates from mutant and wild-type alpha-synuclein proteins and NAC peptide induce apoptotic cell death in human neuroblastoma cells by formation of beta-sheet and amyloid-like filaments. FEBS Lett. 440, 71-75 (1998).
17. Conway, K. A., Harper, J. D. & Lansbury, P. T. Accelerated in vitro fibril formation by a mutant alpha-synuclein linked to early-onset Parkinson disease. Nat. Med. 4, 1318-1320 (1998).
18. Nelson, R. et al. Structure of the cross-beta spine of amyloid-like fibrils. Nature 435, 773-778 (2005).
19. Sawaya, M. R. et al. Atomic structures of amyloid cross-beta spines reveal varied steric zippers. Nature 447, 453-457 (2007).
20. Bodies, A. M., Guthrie, D. J., Greer, B. & Irvine, G. B. Identification of the region of non-Abeta component (NAC) of Alzheimer's disease amyloid responsible for its aggregation and toxicity. J. Neurochem. 78, 384-395 (2001).
21. Nannenga, B. L. & Gonen, T. Protein structure determination by MicroED. Curr. Opin. Struct. Biol. 27C, 24-31 (2014).
22. Nannenga, B. L. eLife (2014). Structure of catalase determined by MicroED. 2014; 3:e03600
23. Yonekura, K., Kato, K., Ogasawara, M., Tomita, M. & Toyoshima, C. Electron crystallography of ultrathin 3D protein crystals: atomic model with charges. Proc. Natl. Acad. Sci. U.S.A. 112, 3368-3373 (2015).
24. Doyle, P. A. & Turner, P. S. Relativistic Hartree-Fock X-ray and electron scattering factors. Acta Crystallogr. Sect. A 24, 390-397 (1968).

25. Der-Sarkissian, A., Jao, C. C., Chen, J. & Langen, R. Structural organization of alpha-synuclein fibrils studied by site-directed spin labeling. J. Biol. Chem. 278, 37530-37535 (2003).
26. Chen, M., Margittai, M., Chen, J. & Langen, R. Investigation of alpha-synuclein fibril structure by site-directed spin labeling. J. Biol. Chem. 282, 24970-24979 (2007).
27. Sarafian, T. A. et al. Impairment of mitochondria in adult mouse brain overexpressing predominantly full-length, N-terminally acetylated human α-synuclein. PloS One 8, e63557 (2013).
28. Caughey, B. & Lansbury, P. T. Protofibrils, pores, fibrils, and neurodegeneration: separating the responsible protein aggregates from the innocent bystanders. Annu. Rev. Neurosci. 26, 267-298 (2003).
29. Danzer, K. M., Schnack, C., Sutcliffe, A., Hengerer, B. & Gillardon, F. Functional protein kinase arrays reveal inhibition of p-21-activated kinase 4 by alpha-synuclein oligomers. J. Neurochem. 103, 2401-2407 (2007).
30. Karpinar, D. P. et al. Pre-fibrillar alpha-synuclein variants with impaired beta-structure increase neurotoxicity in Parkinson's disease models. EMBO J. 28, 3256-3268 (2009).
31. Winner, B. et al. In vivo demonstration that alpha-synuclein oligomers are toxic. Proc. Natl. Acad. Sci. U.S.A. 108, 4194-4199 (2011).
32. Chen, S. W. et al. Structural characterization of toxic oligomers that are kinetically trapped during α-synuclein fibril formation. Proc. Natl. Acad. Sci. U.S.A. 112, E1994-2003 (2015).
33. Bousset, L. et al. Structural and functional characterization of two alpha-synuclein strains. Nat. Commun. 4, 2575 (2013).
34. Auluck, P. K., Caraveo, G. & Lindquist, S. α-Synuclein: membrane interactions and toxicity in Parkinson's disease. Annu. Rev. Cell Dev. Biol. 26, 211-233 (2010).
35. Lee, J. C., Langen, R., Hummel, P. A., Gray, H. B. & Winkler, J. R. Alpha-synuclein structures from fluorescence energy-transfer kinetics: implications for the role of the protein in Parkinson's disease. Proc. Natl. Acad. Sci. U.S.A. 101, 16466-16471 (2004).
36. Sievers, S. A. et al. Structure-based design of non-natural amino-acid inhibitors of amyloid fibril formation. Nature 475, 96-100 (2011).
37. Otwinowski, Z. & Minor, W. in Methods in Enzymology (ed. Charles W. Carter, J.) Volume 276, 307-326 (Academic Press, 1997).
38. Weierstall, U., Spence, J. C. H. & Doak, R. B. Injector for scattering measurements on fully solvated biospecies. Rev. Sci. Instrum. 83, 035108 (2012).
39. Hattne, J. et al. Accurate macromolecular structures using minimal measurements from X-ray free-electron lasers. Nat. Methods 11, 545-548 (2014).
40. Sauter, N. K., Hattne, J., Grosse-Kunstleve, R. W. & Echols, N. New Python-based methods for data processing. Acta Crystallogr. D Biol. Crystallogr. 69, 1274-1282 (2013).
41. Kabsch, W. XDS. Acta Crystallogr. D Biol. Crystallogr. 66, 125-132 (2010).
42. McCoy, A. J. et al. Phaser crystallographic software. J. Appl. Crystallogr. 40, 658-674 (2007).
43. Murshudov, G. N., Vagin, A. A. & Dodson, E. J. Refinement of macromolecular structures by the maximum-likelihood method. Acta Crystallogr. D Biol. Crystallogr. 53, 240-255 (1997).
44. Afonine, P. V. et al. Towards automated crystallographic structure refinement with phenix.refine. Acta Crystallogr. D Biol. Crystallogr. 68, 352-367 (2012).
45. Emsley, P., Lohkamp, B., Scott, W. G. & Cowtan, K. Features and development of Coot. Acta Crystallogr. D Biol. Crystallogr. 66, 486-501 (2010).
46. Delano, W. The PyMOL Molecular Graphics System. (Schrödinger LLC).
47. Jakes, R., Spillantini, M. G. & Goedert, M. Identification of two distinct synucleins from human brain. FEBS Lett. 345, 27-32 (1994).
48. Johnson, M., Coulton, A. T., Geeves, M. A. & Mulvihill, D. P. Targeted amino-terminal acetylation of recombinant proteins in E. coli. PloS One 5, e15801 (2010).
49. Whitelegge, J. P., Zhang, H., Aguilera, R., Taylor, R. M. & Cramer, W. A. Full subunit coverage liquid chromatography electrospray ionization mass spectrometry (LCMS+) of an oligomeric membrane protein: cytochrome b(6)f complex from spinach and the cyanobacterium Mastigocladus laminosus. Mol. Cell. Proteomics MCP 1, 816-827 (2002).
50. Rao, J. N., Jao, C. C., Hegde, B. G., Langen, R. & Ulmer, T. S. A combinatorial NMR and EPR approach for evaluating the structural ensemble of partially folded proteins. J. Am. Chem. Soc. 132, 8657-8668 (2010).
51. Brunger, A. T. Version 1.2 of the Crystallography and NMR system. Nat. Protoc. 2, 2728-2733 (2007).
52. Fabiola, F., Bertram, R., Korostelev, A. & Chapman, M. S. An improved hydrogen bond potential: impact on medium resolution protein structures. Protein Sci. Publ. Protein Soc. 11, 1415-1423 (2002).
53. Comellas, G. et al. Structured regions of α-synuclein fibrils include the early-onset Parkinson's disease mutation sites. J. Mol. Biol. 411, 881-895 (2011).
54. Vilar, M. et al. The fold of alpha-synuclein fibrils. Proc. Natl. Acad. Sci. U.S.A. 105, 8637-8642 (2008).
55. Goldschmidt, L., Teng, P. K., Riek, R. & Eisenberg, D. Identifying the amylome, proteins capable of forming amyloid-like fibrils. Proc. Natl. Acad. Sci. 107, 3487-3492 (2010).
56. Read, R. J. Improved Fourier coefficients for maps using phases from partial structures with errors. Acta Crystallogr. A 42, 140-149 (1986).
57. Eisenberg, D. S. et al. Structure-based design of peptide inhibitors of amyloid fibrillation, U.S. Pat. No. 8,754,034.
58. Eisenberg, D. S. et al. Structure-based peptide inhibitors of p53 aggregation as a new approach to cancer therapeutics; WO 2014/182961 (2014); US2014/037387.
59. The CCP4 suite: programs for protein crystallography. Acta Crystallogr D Biol Crystallogr 50, 760-3 (1994).
60. Lawrence, M. C. & Colman, P. M. Shape complementarity at protein/protein interfaces. J Mol Biol 234, 946-50 (1993).
61. Kyte J, Doolittle R F (May 1983). "A simple method for displaying the hydropathic character of a protein". J. Mol. Biol. 157 (1): 105-32.
62. Warren L. DeLano "The PyMOL Molecular Graphics System." DeLano Scientific LLC, San Clos, Calif., USA.
63. Jiang, L. et al. (2013). Structure-based discovery of fiber-binding compounds that reduce the cytotoxicity of amyloid beta. ELife 2013; 2e00857

From the foregoing description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding embodiments

We claim:

1. A peptide comprising an amino acid sequence of:

GAVVWGVTAVKKGRKKRRQRRRPQ;    (SEQ ID NO: 6)
    or

YGRKKRRQRRRAVVTGVTAVAE.    (SEQ ID NO: 7)

2. The peptide of claim 1, wherein the peptide inhibits α-synuclein aggregation by binding to α-synuclein at residues 68-78 of SEQ ID NO: 1.

3. The peptide of claim 1, wherein the peptide is coupled to a heterologous peptide tag.

4. The peptide of claim 3, wherein the heterologous peptide tag comprises:
   an amino acid sequence that increases peptide solubility; and/or
   an amino acid sequence that facilitates monitoring of the peptide.

5. The peptide of claim 1, wherein at least one of the amino acids in the peptide is substituted with a non-naturally occurring amino acid.

6. The peptide of claim 5, wherein the non-naturally occurring amino acid is selected from a D-amino acid and an amino acid comprising a N-methyl group moiety.

7. A method of treating a neurodegenerative disease in a subject, the method comprising contacting α-synuclein protofilaments in the subject with an effective amount of a peptide of claim 5.

8. The method of claim 7, wherein the peptide is coupled to a heterologous peptide tag.

9. The method of claim 8, wherein the heterologous peptide tag comprises:
an amino acid sequence that increases peptide solubility; and/or
an amino acid sequence that facilitates monitoring of the peptide.

10. The method of claim 7, where the neurodegenerative disease is Alzheimer's disease or an α-synuclein mediated disease.

11. The method of claim 10, wherein the α-synuclein mediated disease is selected from Alzheimer's disease, Parkinson's disease, Lewy body dementia, and multiple system atrophy.

12. A method of modulating one or more of: the size of α-synuclein amyloid fibrils, the rate of growth of α-synuclein amyloid fibrils, or the rate of spread of α-synuclein amyloid fibrils, the method comprising:
contacting the α-synuclein amyloid fibrils with the peptide of claim 1 in an environment where the peptide contacts α-synuclein at residues 68-78 or residues 47-56 of SEQ ID NO:1 such that the contacted α-synuclein amyloid fibrils exhibit one or more of: a modulated size, modulated rate of growth, or modulated rate of spread of α-synuclein amyloid fibrils.

13. A method for reducing or inhibiting α-synuclein aggregation, comprising contacting α-synuclein amyloid fibrils with a peptide of claim 1 in an amount sufficient to reduce or inhibit α-synuclein aggregation.

14. The method of claim 13, wherein the peptide is coupled to a heterologous peptide tag.

15. The method of claim 14, wherein the heterologous peptide tag comprises:
an amino acid sequence that increases peptide solubility; and/or
an amino acid sequence that facilitates monitoring of the peptide.

16. The method of claim 13, wherein the α-synuclein amyloid fibrils are within an in vivo environment.

17. The method of claim 16, wherein α-synuclein aggregation is reduced or inhibited in a subject.

18. The method of claim 17, wherein the subject has a neurodegenerative disease.

19. The method of claim 18, where the neurodegenerative disease is Alzheimer's disease or an α-synuclein mediated disease.

20. The method of claim 19, wherein the α-synuclein mediated disease is selected from Alzheimer's disease, Parkinson's disease, Lewy body dementia, and multiple system atrophy.

* * * * *

SEQUENCE LISTING

<160> NUMBER OF SEQ ID NOS: 56

<210> SEQ ID NO 1
<211> LENGTH: 140
<212> TYPE: PRT
<213> ORGANISM: Homo sapiens

<400> SEQUENCE: 1

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Val Val His Gly Val Thr Thr Val
1               5

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Ala Val Val Trp Gly Val Thr Ala Val Lys Lys
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 4

Arg Ala Val Val Thr Gly Val Thr Ala Val Ala Glu
1               5                   10

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Ala Val Val Trp Gly Val Thr Ala Val Lys Lys Lys Lys Lys
1               5                   10                  15

<210> SEQ ID NO 6
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Ala Val Val Trp Gly Val Thr Ala Val Lys Lys Gly Arg Lys Lys
1               5                   10                  15

Arg Arg Gln Arg Arg Arg Pro Gln
            20

<210> SEQ ID NO 7
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Tyr Gly Arg Lys Lys Arg Arg Gln Arg Arg Arg Ala Val Val Thr Gly
1               5                   10                  15

Val Thr Ala Val Ala Glu
            20

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(16)
<223> OTHER INFORMATION: This sequence may encompass 5-16 residues

<400> SEQUENCE: 8

Arg Arg Arg Arg Arg Arg Arg Arg Arg Arg Arg Arg Arg Arg Arg Arg
1               5                   10                  15

<210> SEQ ID NO 9
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 9

Arg Gly Gly Arg Leu Ser Tyr Ser Arg Arg Phe Ser Thr Ser Thr
1               5                   10                  15

Gly Arg

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Arg Leu Ser Tyr Ser Arg Arg Arg Phe
1               5                   10

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Gln Ile Lys Ile Trp Phe Gln Asn Arg Arg Met Lys Trp Lys Lys
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Gln Ile Arg Ile Trp Phe Gln Asn Arg Arg Met Arg Trp Arg Arg
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Lys Gln Ile Lys Ile Trp Phe Gln Asn Lys Lys Met Lys Trp Lys Lys
1               5                   10                  15

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Arg Lys Lys Arg Arg Gln Arg Arg Arg Pro Trp Gln
1               5                   10
```

```
<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Arg Lys Lys Arg Arg Gln Arg Arg Pro Pro Gln
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Arg Arg Arg Arg Arg Arg Arg Arg Pro Pro Gln
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Tyr Gly Arg Lys Lys Arg Arg Gln Arg Arg Arg
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Arg Lys Lys Arg Arg Gln Arg Arg Arg Pro Pro Gln
1               5                   10

<210> SEQ ID NO 19
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Lys Met Thr Arg Ala Gln Arg Arg Ala Ala Arg Arg Asn Arg Trp
1               5                   10                  15

Thr Ala Arg

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 20

Arg Arg Arg Arg Asn Arg Thr Arg Arg Asn Arg Arg Val Arg
1               5                   10                  15

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Thr Arg Arg Gln Arg Thr Arg Ala Arg Arg Asn Arg
1               5                   10

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Asn Ala Lys Thr Arg Arg His Glu Arg Arg Lys Leu Ala Ile Glu
1               5                   10                  15

Arg

<210> SEQ ID NO 23
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Leu Leu Ile Ile Leu Arg Arg Arg Ile Arg Lys Gln Ala His Ala His
1               5                   10                  15

Ser Lys

<210> SEQ ID NO 24
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 25
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25
```

```
Ala Gly Tyr Leu Leu Gly Lys Ile Asn Leu Lys Ala Leu Ala Ala Leu
1               5                   10                  15

Ala Lys Lys Ile Leu
            20
```

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

```
Pro Ile Arg Arg Arg Lys Lys Leu Arg Arg Leu Lys
1               5                   10
```

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

```
Arg Arg Gln Arg Arg Thr Ser Lys Leu Met Lys Arg
1               5                   10
```

<210> SEQ ID NO 28
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

```
Lys Glu Thr Trp Trp Glu Thr Trp Trp Thr Glu Trp Ser Gln Pro Lys
1               5                   10                  15

Lys Lys Arg Lys Val
            20
```

<210> SEQ ID NO 29
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

```
Lys Glu Thr Trp Phe Glu Thr Trp Phe Thr Glu Trp Ser Gln Pro Lys
1               5                   10                  15

Lys Lys Arg Lys Val
            20
```

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

```
Lys Trp Phe Glu Thr Trp Phe Thr Glu Trp Pro Lys Lys Arg Lys
1               5                  10                 15

<210> SEQ ID NO 31
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Met Asp Ala Gln Thr Arg Arg Arg Glu Arg Arg Ala Glu Lys Gln Ala
1               5                  10                  15

Gln Trp Lys Ala Ala Asn
            20

<210> SEQ ID NO 32
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Thr Ala Lys Thr Arg Tyr Lys Ala Arg Arg Ala Glu Leu Ile Ala Glu
1               5                  10                  15

Arg Arg

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ser Gln Met Thr Arg Gln Ala Arg Arg Leu Tyr Val
1               5                  10

<210> SEQ ID NO 34
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Thr Arg Arg Asn Lys Arg Asn Arg Ile Gln Glu Gln Leu Asn Arg Lys
1               5                  10                  15

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Lys Leu Ala Leu Lys Leu Ala Leu Lys Leu Ala Leu Ala Leu Lys Leu
1               5                  10                  15
```

Ala

```
<210> SEQ ID NO 36
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Met Gly Leu Gly Leu His Leu Leu Val Leu Ala Ala Leu Gln Gly
1               5                   10                  15

Ala Trp Ser Gln Pro Lys Lys Lys Arg Lys Val
            20                  25

<210> SEQ ID NO 37
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25

<210> SEQ ID NO 38
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 39
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25

<210> SEQ ID NO 40
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 40

Thr Arg Gln Ala Arg Arg Asn Arg Arg Arg Trp Arg Glu Arg Gln
1               5                   10                  15

Arg

<210> SEQ ID NO 41
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (22)..(22)
<223> OTHER INFORMATION: Any amino acid

<400> SEQUENCE: 41

Glu Glu Glu Glu Glu Asp Asp Asp Asp Lys Ala Xaa Arg Arg Arg
1               5                   10                  15

Arg Arg Arg Arg Arg Xaa Cys
                20

<210> SEQ ID NO 42
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (21)..(21)
<223> OTHER INFORMATION: Any amino acid

<400> SEQUENCE: 42

Glu Glu Glu Glu Glu Asp Asp Asp Asp Lys Ala Arg Arg Arg Arg
1               5                   10                  15

Arg Arg Arg Arg Xaa Cys
                20

<210> SEQ ID NO 43
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (18)..(18)
<223> OTHER INFORMATION: Any amino acid

<400> SEQUENCE: 43

Glu Asp Asp Asp Asp Lys Ala Xaa Arg Arg Arg Arg Arg Arg Arg
1               5                   10                  15

Arg Xaa Cys

<210> SEQ ID NO 44
```

```
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (19)..(19)
<223> OTHER INFORMATION: Any amino acid
<220> FEATURE:
<221> NAME/KEY: MOD_RES
<222> LOCATION: (22)..(22)
<223> OTHER INFORMATION: Any amino acid

<400> SEQUENCE: 44

Glu Glu Asp Asp Asp Asp Lys Ala Arg Xaa Arg Arg Xaa Arg Arg Xaa
1               5                   10                  15

Arg Arg Xaa Arg Arg Xaa Cys
            20

<210> SEQ ID NO 45
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Any amino acid

<400> SEQUENCE: 45

Asp Asp Asp Asp Asp Asp Lys Ala Arg Arg Arg Arg Arg Arg Arg
1               5                   10                  15

Arg Xaa Cys

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Ala Val Val Thr Gly Val Thr Ala Val Ala
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47
```

```
Gly Val Val His Gly Val Thr Thr Val Ala
1               5                   10

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ala Val Val Thr Gly Val Thr Ala Val
1               5

<210> SEQ ID NO 49
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Val Thr Thr Val
1               5

<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Val Thr Ala Val
1               5

<210> SEQ ID NO 51
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gln Val Thr Asn Val Gly
1               5

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gln Lys Thr Val Glu Gly
1               5

<210> SEQ ID NO 53
<211> LENGTH: 6
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 53

Gly Val Thr Thr Val Ala
1               5

<210> SEQ ID NO 54
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: nme-Gly

<400> SEQUENCE: 54

Tyr Gly Arg Lys Lys Arg Arg Gln Arg Arg Ala Val Val Thr Gly
1               5                   10                  15

Val Thr Ala Val Ala Glu
            20

<210> SEQ ID NO 55
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(16)
<223> OTHER INFORMATION: This sequence may encompass 5-16 residues

<400> SEQUENCE: 55

Lys Lys Lys Lys Lys Lys Lys Lys Lys Lys Lys Lys Lys Lys Lys Lys
1               5                   10                  15

<210> SEQ ID NO 56
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (6)..(16)
<223> OTHER INFORMATION: This sequence may encompass 1-16 residues

<400> SEQUENCE: 56

Asp Asp Asp Asp Asp Asp Asp Asp Asp Asp Asp Asp Asp Asp Asp Asp
1               5                   10                  15
```